(12) United States Patent
Rybczynski et al.

(10) Patent No.: US 8,487,110 B2
(45) Date of Patent: Jul. 16, 2013

(54) METHOD FOR PREPARING ISOFAGOMINE AND ITS DERIVATIVES

(75) Inventors: Philip Rybczynski, Branchburg, NJ (US); Alexander Tretyakov, Fox Point, WI (US); Dan Fuerst, Menomonee Falls, WI (US); Kamlesh Sheth, North Brunswick, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 387 days.

(21) Appl. No.: 12/624,260

(22) Filed: Nov. 23, 2009

(65) Prior Publication Data

US 2010/0160638 A1 Jun. 24, 2010

Related U.S. Application Data

(63) Continuation-in-part of application No. PCT/US2008/064559, filed on May 22, 2008.

(60) Provisional application No. 60/939,519, filed on May 22, 2007.

(51) Int. Cl.
*A61K 31/445* (2006.01)

(52) U.S. Cl.
USPC ........................................................ 546/242

(58) Field of Classification Search
USPC ........................................................ 546/242
See application file for complete search history.

(56) References Cited

U.S. PATENT DOCUMENTS

| 5,844,102 | A | 12/1998 | Sierks et al. | |
|---|---|---|---|---|
| 7,501,439 | B2 * | 3/2009 | Mugrage et al. | 514/315 |
| 2004/0019198 | A1 | 1/2004 | Crich et al. | |
| 2006/0247222 | A1 | 11/2006 | Pinto et al. | |
| 2007/0065922 | A1 | 3/2007 | Barai et al. | |

FOREIGN PATENT DOCUMENTS

WO WO 2005/046612 5/2005

OTHER PUBLICATIONS

Hense et. al. "Direct preparation of diacetals from 1,2-diketones and their use as 1,2-diol protecting groups" J. Chem. Soc., Perkin Trans. 1, 1997 2023.*
Zhu "Rational Design and Synthesis of Highly Potent b-Glucocerebrosidase Inhibitors" Angew. Chem. Int. Ed. 2005, 44, 7450-7453.*
Goddard-Borger, et. al. "An Expeditious Synthesis of Isofagomine." Australian Journal of Chemistry, 2007, 60(3), 211-213 Published online: Apr. 2, 2007.*
Best, et al., "The Synthesis of a Carbohydrate-like Dihydrooxazine and Tetrahydrooxazine as Putative Inhibitors of Glycoside Hydrolases: A Direct Synthesis of Isofagomine", Can. J. Chem. 80: 857-865, Jun. 21, 2002.
International Search Report for PCT/US08/064559, Aug. 6, 2008.
Andersch et al., "Efficient Synthesis of Isofagomine and Noeuromycin", *Chemistry European Journal*, 7(17):3744-3747, 2001.
Ichikawa et al., "1-$N$-Iminosugars: Potent and selective Inhibitors of β-Glycosidase", *Journal of the American Chemical Society*, 120:3007-3018, 1998.
Shing et al., "Experimental and theoretical Studies on Stereo-and Regioselectivity in Intramolecular Nitrone-Alkene Cycloaddition of Hept-6-enoses Derived from Carbohydrates", *Journal of Organic Chemistry*, 71(8):3253-3263, 2006.
Shing et al., "Arabinose-Derived Ketones as Catalysts for asymmetric Epoxidation of Alkenes", *Journal of Organic Chemistry*, 70(18):7279-7289, 2005.
Zegrocka et al., "Formation of β-lactams fused to the pyranoid ring via the Mitsunobu reaction", *Carbohydrate Research*, 307( I ):33-43, 1998.
Zhu et al., "Rational Design and Synthesis of Highly Potent β-Glucocerebrosidase Inhibitors", *Angewandte Chemie, International Edition*, 44:7450-7453, 2005.
Supplementary Search Report for EP 08 79 5866, dated Dec. 21, 2011.
Meloncelli, et al., "Improvements to the Synthesis of Isofagomine, Noeuromycin, Azafagomine, and Isofagomine Lactam, and a Synthesis of Azanoeuromycin and 'Guanidine' Isofagomine", *Australia Journal of Chemistry*, 59(1):827-833 (2006).

* cited by examiner

*Primary Examiner* — David K O Dell
(74) *Attorney, Agent, or Firm* — Baker Botts L.L.P.

(57) ABSTRACT

A method for preparing isofagomine, its derivatives, intermediates and salts thereof using novel processes to make isofagomine from D-(−)-arabinose and L-(−)-xylose.

10 Claims, No Drawings

METHOD FOR PREPARING ISOFAGOMINE AND ITS DERIVATIVES

CROSS-REFERENCE TO RELATED APPLICATIONS

This application is continuation in part of International Application PCT/US08/064,559, filed May 22, 2008, published Nov. 27, 2008, which claims the benefit of U.S. Provisional Application Ser. No. 60/939,519, filed May 22, 2007, each of which is are hereby incorporated by reference in its their entirety herein.

FIELD OF THE INVENTION

The present invention provides novel processes and intermediates to manufacture isofagomine, its derivatives and their salts for use as pharmaceutical compositions.

BACKGROUND

Iminosugars are potent inhibitors of glycosidases. Azasugars of the isofagomine family are inhibitors of configuration-retaining β-glycosidases due to the formation of a strong electrostatic interaction between a protonated endocyclic nitrogen at the anomeric center of the imino sugar and the catalytic nucleophile of the enzyme. The inhibitors mimic the transition state in the hydrolysis of the glycosidic bond. Isofagomine, (3R,4R,5R)-3,4-dihydroxy-5-hydroxymethylpiperidine, also known as IFG, is one glycosidase inhibitor which was synthesized in anticipation that it would be effective as a liver glycogen phosphorylase inhibitor for the treatment of diabetes (see U.S. Pat. Nos. 5,844,102 to Sierks et al., and 5,863,903 to Lundgren et al., both of which are herein incorporated by reference).

IFG Tartate Salt, its production and its use to treat Gaucher Disease has also been described in U.S. patent application Ser. No. 11/752,658, which is hereby incorporated by reference.

IFG and IFG Derivatives

IFG and/or N-alkylated IFG derivatives are described in the following: U.S. Pat. Nos. 5,844,102 to Sierks, 5,863,903 to Lundgren, and 6,046,214 to Kristiansen et al.; Jespersen et al., *Angew. Chem., Int ed. Engl.* 1994; 33: 1778-9; Dong et al., *Biochem.* 1996; 35:2788; Lundgren et al., *Diabetes.* 1996; 45:S2 521; Schuster et al., *Bioorg Med Chem. Lett.* 1999; 9(4):615-8; Andersch et al., *Chem. Eur. J.* 2001; 7: 3744-3747; Jakobsen et al., *Bioorg Med. Chem.* 2001; 9: 733-44; 36:435; Pandy et al., *Synthesis.* 2001: 1263-1267; Zhou et al., *Org. Lett.* 2001; 3(2):201-3; Best et al., *Can. J. Chem./Rev. Can. Chim.* 2002; 80(8): 857-865; Huizhen et al., *J. Carbohydr Chem.* 2004; 23: 223-238; Mehta et al., *Tetrahedron Letters* 2005; 41(30):5747-5751; Ouchi et al., *J Org. Chem.* 2005; 70(13):5207-14; and most recently, Meloncelli et al., *Australian Journal of Chemistry.* 2006; 59 (11) 827-833. Synthesis of the L stereoisomer is described in Panfil et al., *J. Carbohydr Chem.* 2006; 25: 673-84. All of the references in this paragraph are herein incorporated by reference.

Briefly, Jespersen first described synthesis of IFG in a six step synthesis starting from 1,6:2,3-dianhydro-4-O-benzyl-β-D-mannopyranose. This method employed introducing a hydroxymethyl group at C-7 by epoxide opening with vinylmagensium bromide, followed by ozonolysis in ethanol to give 1,6-anhydro-4-O-benzyl-β-D-glucopyranose. Hydrolysis of the anhydro bond with sulfuric acid and oxidative carbon chain cleavage provided a pentodialdose, which was cyclized by reductive amination with ammonia to produce the 4-O-benzyl derivative of IFG. The protecting group was removed by hydrogenation under acid conditions (hydrogen and palladium-on-carbon) to produce the HCl salt of IFG.

Dong et al., described synthesis of disaccharide derivatives of IFG.

Jakobsen described synthesis of IFG and N-substituted IFG derivatives from acrolein, and preparation of N-alkyl derivatives by direct alkylation of 3-O benzylated IFG. Such N-alkyl derivatives include N-methyl, butyl, allyl, propyn-3-yl, 1-dodecyl, acetyl, $CH_2CH_2COOH$, benzyl, $CH_2CH_2Ph$, $NO_2PhCH_2CH_2$, $CH_2CH_2CH_2$-Ph, cyclohexylprop-3-yl, and $CH_2CH=CHPh$.

Pandey described cyclization of PET-generated α-trimethylsilylmethylamine radical cation to a tethered acetylene moiety, for the generation of an aminomethyl group next to a stereocenter (1-[Benzyl(trimethylsilyl-methyl)amino]-1,4,5-trideoxy-2,3-O-(1-methylethylidene)-threo-pent-4-ynitol), starting from tartaric acid, in the synthesis of 1-N-iminosugar type glycosidase inhibitors, including isofagomine.

Andersch and Bols described IFG synthesis starting from D-arabinose by applying a C-4 oxidation method to benzyl α-D-arabino-pyranoside. Subsequent Henry reaction of the obtained aldoketose with nitromethane provided the required branched carbohydrate precursors, which resulted in IFG (17-21% overall yield).

Best et al. described synthesis of IFG from D-xylose, which converted to benzyl 2,3-O-isopropylidene-β-L-xylopyranoside via a derived imidazylate, which was then converted into a nitrile that, upon reduction and protecting-group manipulations, gave benzyl 4-C-aminomethyl-4-deoxy-α-D-arabinoside. Reductive amination with hydrogen and palladium-on-carbon resulted in isofagomine HCl.

Huizhen described synthesis of IFG analogues (3R,4R, 5R)—N-(2-phosphonoethyl)-3,4-dihydroxy-5-hydroxymethyl-piperidine, (3R,4R,5R)—N-(2-phosphonoethyl)-3,4-dihydroxy-5-hydroxy-methylpiperidine, and (3R,4R,5R)—N-(10-chloro-9-anthracenemethyl)-3,4-dihydroxy-5-hydroxy-methylpiperidine by direct alkylation of the corresponding azasugar.

Ouchi et al. described synthesis of 1-azasugars including IFG starting from N-Boc-5-hydroxy-3-piperidine via stereoselective epoxidation of and intermediate tert-butyldiphenyl-silylcholoride vinyl derivative, followed by oxidative cleavage of the vinyl group to an aldehyde, followed by reduction and deprotection to produce IFG.

Schuster et al. disclosed methyl- and hydroxymethyl derivatives of IFG which were generated via aldolase-catalyzed C—C bond formation.

Mehta et al. described stereoselective synthesis of isofagomine analogues from a suitably functionalized cyclopentene intermediate extracted from the norbornyl framework. Double reductive amination or inter- and intramolecular N-alkylations are the key steps in constructing the piperidine ring. Isofagomine derivatives exhibit moderate inhibitory activity in enzyme assays.

Ouchi et al. describe synthesis of IFG from chiral N-Boc-5-hydroxy-3-piperidene via stereoselective epoxidation and regioselective ring-cleavage in a highly stereo-controlled manner.

Zhou et al. describe synthesis of IFG by 1,2-reduction of substituted pyridines beginning with methyl nicotinate.

IFG for the Treatment of Diseases

Isofagomine and related compounds have been shown to be effective at increasing the activity of the lysosomal enzyme β-glucocerebrosidase (also known as GCase) See U.S. Pat. Nos. 6,158,583, 6,916,839, and 7,141,582, and U.S. patent application Ser. Nos. 10/988,428, and 10/988,427, both filed Nov. 12, 2004 (all of which are herein incorporated by reference). It was unexpectedly found that specific enzyme inhibitors could bind with specificity to the enzyme during its synthesis, stabilizing protein folding in the ER, but could dissociate from the enzyme at its native location in the lysosome, thereby increasing enzyme activity by increasing the level of enzyme that is processed instead of degraded. IFG, an inhibitor of GCase, binds in the active site of both wild-type and mutant GCase and stabilizes the enzyme during synthesis and processing (Steet et al., *Biochem Pharmacol.* 2007; 73(9):1376-83; Lieberman et al., *Nature Chem. Biol.* 2007; 3(2):101-7). Because IFG can dissociate from the active site, the net effect of IFG binding is an increase in GCase processing, trafficking to the lysosome, and activity.

Importantly, IFG has been shown to restore processing, trafficking and activity to of mutant forms of GCase which are unstable due to missense mutations and become degraded. In the absence of the "pharmacological chaperone," the mutated enzyme protein misfolds in the ER (Ishii et al., *Biochem. Biophys. Res. Comm.* 1996; 220: 812-815), is retarded in its maturation to a final product, and is subsequently degraded by the ER-associated degradation mechanism. Homozygous mutant GCase is associated with the lysosomal storage disease Gaucher disease. In vitro, IFG was shown to increase the activity of mutant GCase in fibroblasts from Gaucher patients (See U.S. Pat. Nos. 6,583,158, 6,916,829 and 7,141,582 all of which are herein incorporated by reference). In vivo, treatment with IFG increases GCase activity and improves the phenotype in a mouse model of Gaucher disease expressing mutations in the β-glucocerebrosidase gene (Gba) gene (unpublished data). Recently, IFG tartrate has been shown to increases the activity of human GCase in healthy volunteers up to 3.5 fold in Phase 1 clinical trials. In Phase 2 clinical trials IFG tartrate has also shown an increase in GCase activity in Gaucher patients expressing certain missense mutations that create misfolded GCase.

In addition, there is a well-established link between mutations in the gene encoding and Parkinson's disease. In one study, patients with rare, early onset, treatment-resistant parkinsonism were found to have at least one allele with a Gba missense mutation, including homozygous and heterozygous individuals for N370S, a mutation typically associated with type 1, non-neuronopathic disease (Tayebi et al., *Mol. Genet. Metab.* 2003; 79; 104-109). In another study, Ashkenazi Jews with idiopathic Parkinson's disease were evaluated for six Gba mutations (N370S, L444P, 84GG, V394L, and R4961-1) with the majority being heterozygous for known Gba mutations (Aharon-Peretz et al., *New Eng. J. Med.* 2004; 351: 1972-77). Parkinson's and Gaucher diseases also share some pathological features, including neuronal loss, astrogliosis, and the presence of cytotoxic Lewy-body-like α-synuclein inclusions in hippocampal neurons (the CA2-4 region) (Wong et al., *Mol. Genet. Metabol.* 2004; 38: 192-207).

SUMMARY OF THE INVENTION

The present invention provides a method for preparing isofagomine, its derivatives, or acid salts thereof, comprising protecting the anomeric hydroxyl group of D-(−)-arabinose with a protecting group to form a glycoside; protecting the 2- and 3-hydroxyl groups of said glycoside using a 1,2-dione to form a triprotected arabinose derivative; converting said arabinose derivative to a triprotected xylose derivative; converting said xylose derivative to a triprotected nitrile; converting said nitrile to a protected diol and deprotecting said diol.

In another embodiment, the invention optionally comprises a step converting said arabinose derivative to said xylose derivative through an activated system wherein the activated system is optionally isolated before conversion. In another embodiment the invention optionally comprises a step of converting said xylose derivative to said nitrile using an activated system, wherein the activated system is optionally isolated before conversion followed by displacement by a cyano source.

In another embodiment, the invention optionally comprises a obtaining said nitrile after purifying said xylose derivative.

In another embodiment, the invention optionally comprises converting said arabinose derivative to said xylose derivative by a Mitsunobu inversion reaction to form an inverted ester derivative and saponification.

In another embodiment, the invention provides a method for preparing isofagomine, its derivatives, or acid salts thereof, comprising protecting the anomeric hydroxyl group of D-(−)-arabinose with a protecting group to form a glycoside; protecting the 2- and 3-hydroxyl groups of said glycoside using a 1,2-dione to form a triprotected arabinose derivative; converting said arabinose derivative to a triprotected xylose derivative; converting said xylose derivative to a triprotected nitrile; converting said nitrile to a protected isofagomine salt and deprotecting said isofagomine salt.

In yet another embodiment, the invention provides a method for preparing isofagomine, its derivatives, or acid salts thereof, comprising protecting the anomeric hydroxyl group of D-(−)-arabinose with a protecting group to form a glycoside; protecting the 2- and 3-hydroxyl groups of said glycoside using a 1,2-dione to form a triprotected arabinose derivative; converting said arabinose derivative to a triprotected xylose derivative; converting said xylose derivative to a triprotected nitrile; reducing said nitrile to a triprotected primary amine; deprotecting said primary amine to a diol and using catalytic hydrogenation.

In another embodiment, the invention provides a method for preparing isofagomine, its derivatives, or acid salts thereof, comprising protecting the anomeric hydroxyl group of D-(−)-arabinose with a protecting group to form a glycoside; further protecting by converting said protected glycoside to an acetonide using a ketal or ketone; converting said acetonide to an alkoxide and reacting with an alkylating agent to form an ether; converting said ether to a diol having protecting two protecting groups; further protecting said diol using selective etherification to form a triprotected arabinose derivative; converting said arabinose derivative to a triprotected xylose derivative using an activated system; converting said xylose derivative to a triprotected nitrile using an activated system; converting said nitrile using catalytic hydrogenation.

In another embodiment, the invention provides a method for preparing isofagomine, its derivatives, or acid salts thereof, comprising contacting L-(−)-xylose with an alcohol, an activating agent and optionally a solvent to form a protected glycoside; converting said glycoside to a triprotected xylose derivative; converting said xylose derivative to a triprotected nitrile; converting said nitrile to a protected diol and deprotecting said diol.

In another embodiment, the invention provides a compound of the formula

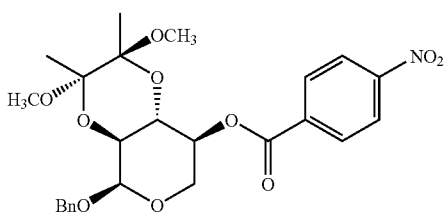 [SMILES: CO[C@@]1(C)O[C@@H]2[C@H](OCc3ccccc3)OC[C@H](OC(=O)c3ccc([N+](=O)[O-])cc3)[C@H]2O[C@]1(C)OC]

and a method of using this compound to make isofagomine, its derivatives, or acid salts thereof.

In yet another embodiment, the invention provides a method for preparing the L-(+) tartaric acid salt of isofagomine. In one embodiment a method is provided to prepare the L-(+) tartaric acid salt of isofagomine represented by the structure:

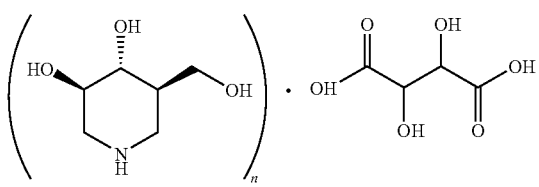

wherein n is 1 or 2. In one embodiment, n is 1.

DETAILED DESCRIPTION

Definitions

The terms and abbreviations used in this specification generally have their ordinary meanings in the art, within the context of this invention and in the specific context where each term is used. Certain terms and abbreviations are discussed below, or elsewhere in the specification, to provide additional guidance to the practitioner in describing the methods and compositions of the invention.

"CsF" means cesium fluoride.
"DMA" means N,N-dimethylaniline.
"DMF" means N,N-dimethylformamide.
"NMP" means N-methylpyrrolidone.
"DMSO" means dimethylsulfoxide.
"LG" means Leaving Group
"MTBE" means methyl tert butyl ether.
"Pd/C" means palladium on carbon.
"Pd(OH)$_2$/C" means palladium hydroxide on carbon in any of its various forms including Pearlman's catalyst or any of the manifestations called Degussa catalyst.
"PG" and "PG$^2$" means a hydroxyl protecting group.
"PtO$_2$" means platinum oxide, including hydrated forms.
"THF" means tetrahydrofuran.
"TLC" means thin-layer chromatography.
"Bn" means benzyl.

The term "hydroxyl protecting group" or "PG" or "PG$^2$" includes any common protecting group for hydroxyl known to those of ordinary skill in the art to avoid undesired reactions, such as, but not limited to, 4-methoxybenzyl, benzyl, trimethylsilyl, acetals, ketals and fused diketals. "PG" and "PG$^2$" may be the same or different.

The term "leaving group" or LG includes leaving groups known to those of ordinary skill in the art, such as, but not limited to alkyl and aryl sulfonates (such as benzenesulfonate, tosylate, mesylate), halides (such as I, Br, and Cl), carboxylates (such as acetates, and trifluoroacetates) and cyanate (such as thiocyanate) groups.

The abbreviation "IFG" means isofagomine or (3R,4R,5R)-3,4-dihydroxy-5-hydroxymethyl-piperidine. IFG has molecular formula C$_6$H$_{13}$NO$_3$ and a molecular weight of 147.17. IFG is described in U.S. Pat. Nos. 5,844,102 to Sierks et al. and 5,863,903 to Lundgren et al., both of which are hereby incorporated by reference, and has the following structure:

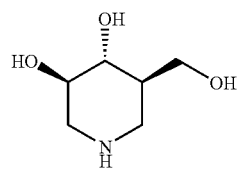

IFG
Isofagomine
(3R, 4R, 5R)-3,4-dihydroxy-5-hydroxymethyl-piperidine

IFG derivatives includes molecules that can be prepared from IFG using a general chemical reaction technology that is known to one of skill in the art at the time of the filing of this application.

As used herein, substituted alkyl refers to alkyl groups wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl), As used herein, substituted cycloalkyl refers to cycloalkyl substituted with an alkyl group, wherein alkyl is as defined above or a group wherein one or more of the hydrogen atoms has been replaced by a halogen, oxygen, hydroxy, amine (primary), amine (secondary-alkyl substituted by alkyl as above), amine (tertiary-alkyl substituted by alkyl as defined above), sulfur, —SH or phenyl, As used herein, substituted aryl refers to an aryl ring substituted with one or more substituents selected from the group consisting of alkyl, alkenyl, alkynyl, halo, alkoxy, acyloxy, amino, hydroxy, carboxy, cyano, nitro, alkylthio and thioalkyl where alkyl thio refers to the group —S-alkyl and thioalkyl refers to an alkyl group having one or more —SH groups.

Synthesis of IFG and IFG Derivatives

Synthesis of IFG through D-arabinose protected with a 1,2-dione

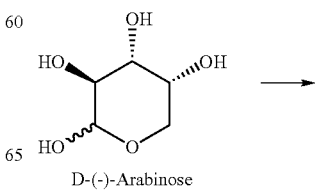

D-(-)-Arabinose

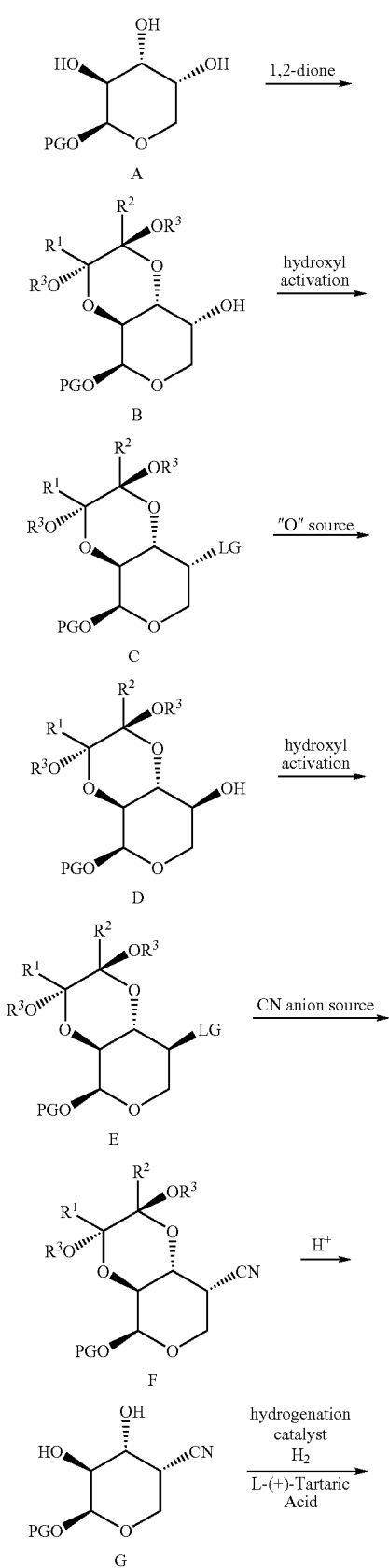

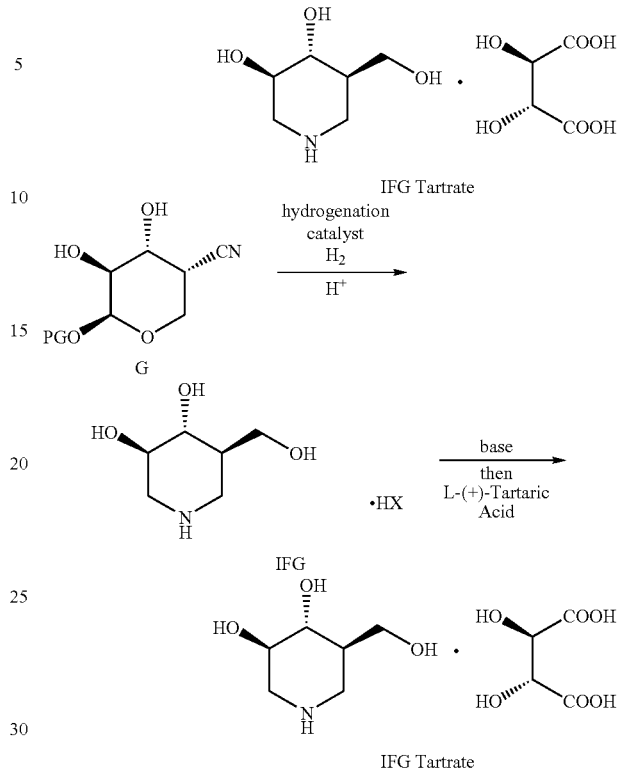

wherein $R_1$ and $R_2$ are independently substituted or unsubstituted alkyl (e.g. $C_1$-$C_6$ alkyl), substituted or unsubstituted aryl (eg. benzyl or napthyl), or together $R_1$ and $R_2$ can form a substituted or unsubstituted cycloalkyl such as a cyclohexane (from cyclohexanedione starting material).

D-Arabinose can be converted to the corresponding protected glycoside (A) using an appropriate alcohol with or without solvent (neat reaction), and an activating agent. For instance the range of alcohols that can be used for the hydroxy group includes benzyl alcohol, substituted benzyl alcohols such as methoxybenzyl alcohol, chlorobenzyl alcohol, diphenylmethanol, substituted diphenylmethanols, methanol, ethanol, isopropanol, cyclohexylmethyl alcohol and the like. The protection reaction may be performed with or without a solvent, such as methylene chloride, chloroform, THF, dioxane, DMF, DMA, NMP or mixtures thereof. The activating agent may include HCl, HBr, $H_2SO_4$, some other mineral acid, acetyl chloride, propionyl chloride, or another acid chloride of a carboxylic acid. The reaction can be run at temperatures ranging from about ambient temperature to about 100° C., for times ranging from about 2 to 48 h. Benzyl or substituted benzyl alcohols are preferred, and benzyl alcohol is more preferred. Preferred solvents include dioxane, THF or neat reaction, and more preferred is neat reaction. Preferred activating agents include acetyl chloride and $H_2SO_4$, and more preferred is acetyl chloride. Pure product can be readily isolated by precipitation with a non-polar solvent. The preferred solvent and temperature for this product is methyl-t-butyl ether at ambient temperature.

The glycoside (A) can be further protected as a diketal (B) by reaction with a 1,2 dione or the dialkylketal thereof in the presence of a protic acid or a Lewis acid and an alcohol that may also act as the solvent. For instance, aliphatic or aromatic diones such as 1,2-butanedione, 1,2-cyclohexanedione, 1,2-diphenylethanedione, or 9,10-phenanthrenequinone, or their corresponding ketals, can react with a vicinal diol in the presence of a protic acid such as HCl, $H_2SO_4$, camphorsulfonic acid, p-toluenesulfonic acid, or a Lewis acid such as boron trifluoride etherate or titanium tetrachloride. An alcohol such as methanol, ethanol, isopropanol, the like, and mixtures thereof may be used as a solvent. Preferred conditions for this reaction are 1,2-butanedione or 1,2-cyclohexanedione, in methanol at ambient temperature to 35° C., with camphorsulfonic acid or boron trifluoride etherate. More preferred conditions are 1,2-butanedione in methanol at 35° C. with camphorsulfonic acid. Pure product may be readily obtained, for example, by crystallization from isopropanol, isopropanol and heptane, or ethyl acetate and heptane.

The triprotected intermediate arabinose derivative (B) can be directly converted to the corresponding xylose derivative (D) through an activated system (C) where LG represents a Leaving Group. The route involves activation of the arabinose hydroxyl to a discreet, isolable activated system (C) followed by displacement with inversion using an oxygen source as indicated below. The activated system (C) may be or may not be isolated to be converted to the xylose derivative (D). The hydroxy group of the compound B may be activated with an ester such as p-toluenesulfonate, methanesulfonate, trifluoromethanesulfonate, and the like, formed from the corresponding anhydride or sulfonyl chloride in the presence of an organic base such as pyridine, collidine, Hunig's base, triethylamine, in a non-polar solvent such as methylene chloride, chloroform, or toluene at temperatures from about −20° C. to about ambient temperature. Preferred conditions use p-toluenesulfonyl chloride or trifluoromethanesulfonic anhydride and pyridine in methylene chloride at −20° C. followed by isolation of the sulfonate ester without purification. More preferred conditions use trifluoromethanesulfonic anhydride and pyridine in methylene chloride at −20° C. followed by isolation of the triflate without purification. Displacement with inversion of the configuration can be accomplished with oxygen nucleophiles, preferably alkali or earth alkali metal nitrite or tetraalkylammonium nitrite in solvents commonly used for this type of reaction, e.g., methylene chloride, acetone, THF, DMF, DMA, NMP, and the like at temperatures from about 0° C. to about 40° C. Preferred conditions for displacement of the triflate are sodium or potassium nitrite in DMF at ambient temperature, or displacement with tetramethylammonium, tetraethylammonium, tetrapropylammonium, or tetrabutylammonium nitrite in DMF, or acetone. More preferred conditions are sodium or potassium nitrite in DMF at ambient temperature or tetraethylammonium nitrite in acetone at ambient temperature. In another embodiment of this invention where the conversion is run without isolation of the activated system (C), preferred conditions use trifluoromethanesulfonic anhydride and pyridine in methylene chloride at −20° C. followed by destruction of unreacted anhydride with isopropanol, dilution with acetone, and addition of tetraethylammonium or tetrabutylammonium nitrite at ambient temperature. Purified product can be readily obtained by crystallization from a two solvent system using a polar and a non-polar component. The preferred crystallization solvents for this reaction are isopropanol and heptane.

The triprotected xylose derivative of general formula (D) can be converted into the nitrile compound (F) with inversion of configuration through an activated system. Similar to the method described above, the route involves activation of the xylose hydroxyl to a discreet, isolable activated system (E) followed by displacement by a cyano source. The nitrile compound (F) may also be obtained from the xylose derivative (D) without isolation of the activated system (E). The hydroxy group of the xylose derivative may be activated with an ester such as p-toluenesulfonate, methanesulfonate, trifluoromethanesulfonate, and the like, formed from the corresponding anhydride or sulfonyl chloride in the presence of a mild organic base, such as pyridine, collidine, Hunig's base, triethylamine, and the like in a non-polar solvent such as methylene chloride, chloroform, or toluene at temperatures from about −20° C. to about ambient temperature. Preferred conditions use p-toluenesulfonyl chloride or trifluoromethanesulfonic anhydride and pyridine in methylene chloride at −20° C. followed by isolation of the triflate without purification. More preferred conditions use trifluoromethanesulfonic anhydride and pyridine in methylene chloride at −20° C. followed by isolation of the triflate without purification. Displacement with inversion of configuration can be accomplished preferably with reagents such as alkali or earth alkali metal cyanides, or tetraalkylammonium cyanides in polar, aprotic solvents such as THF, DMF, DMA, NMP, DMSO, and the like at temperatures from about 0° C. to about 40° C. Preferred conditions for displacement of the triflate use tetraethylammonium cyanide in THF at ambient temperature. When the conversion is conducted without isolation of the activated system (E), preferred conditions use trifluoromethanesulfonic anhydride and pyridine in methylene chloride at −20° C. followed by destruction of unreacted anhydride with isopropanol, dilution with THF, and addition of tetraethylammonium cyanide at ambient temperature Purified product may be obtained by extraction followed by crystallization from an alcoholic solvent with or without a non-polar solvent such as hexane, heptane, or toluene. The preferred solvent system is isopropanol and heptane The nitrile (F) can be obtained from the arabinose derivative (B) without purification of the xylose derivative (D).

A nitrile of the general formula (F) can be converted into a diol of the general formula (G) with an acid in water or an aqueous co-solvent system. The acid may include trifluoroacetic acid, trifluoromethanesulfonic acid, and the like. The deprotection can be carried out in water at room temperature for about 2 to about 24 h. Trituration from a non-polar solvent can readily provide the diol. Alternatively, the product (G) can be crystallized from solvent systems such as alcohols or ethyl acetate, with or without a non-polar solvent such as hexane, heptane, or toluene. Preferred conditions for this reaction are water and trifluoroacetic acid at room temperature for 16 h followed by solvent evaporation and heptane trituration of the reaction product.

Conversion of a nitrile intermediate of the general formula (G) to isofagomine acid salt can be carried out in one step by proper choice of protecting groups (e.g. benzyl or 4-methoxybenzyl groups). Nitrile reduction, deprotection at the anomeric center, ring closure, and hydrogenation of the cyclic imine can be accomplished in a single step under hydrogenation conditions to provide isofagomine acid salt in high yield. Catalytic hydrogenation can be carried out with a variety of common catalysts used for such hydrogenation including Pd/C, Pd(OH)$_2$/C, PtO$_2$, Pd(OAc)$_2$ or a combination of catalysts at loadings of 1% to 20%, under hydrogen gas pressure ranging from 14 psi to 100 psi, in protic or aprotic polar solvents, preferably an alcohol such as methanol, ethanol, isopropanol, with or without water co-solvent. Esters such as isopropyl acetate, ethyl acetate or methyl acetate can also be used. The hydrogenation can be carried out in the presence of a mineral acid such as HCl, HBr, HClO$_4$, H$_3$PO$_4$, H$_2$SO$_4$, or a carboxylic acid such as tartaric acid or acetic acid. Note that acetic acid can serve as the solvent as well, with or without water as the co-solvent. The hydrogenation can be run for short or extended periods of time as dictated by the rate of conversion. Preferred conditions use Pd(OH)$_2$/C with loadings of 5% to 20% under pressures from 40 psi to 100 psi in an alcoholic solvent and water with HCl, acetic acid, or tartaric acid. More preferred conditions are 20% loading Pd(OH)$_2$/C under 80 psi hydrogen gas in isopropanol and water with L-(+)-tartaric acid. If isofagomine is formed as the hydrochloride or some other acid salt, it can be converted to the free base and then to the tartrate salt. This method also serves to purify isofagomine from any salt form, including the tartrate.

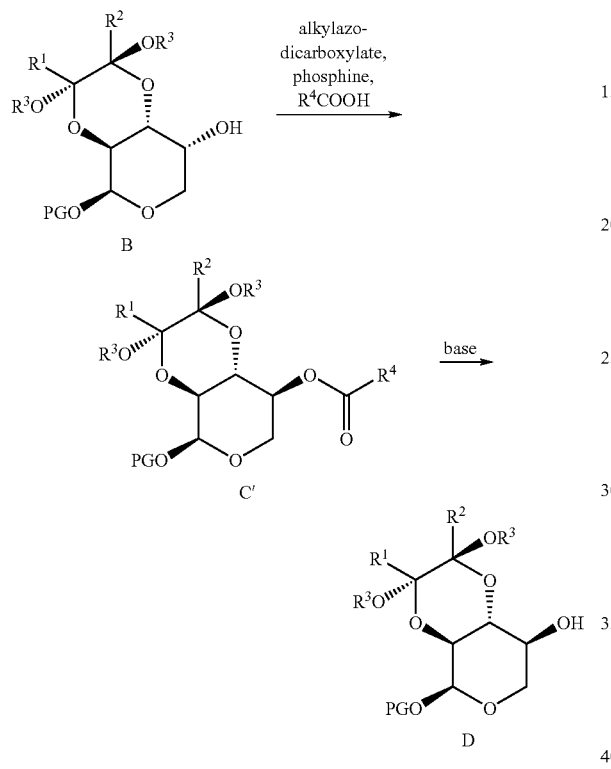

The intermediate arabinose derivative (B) can also be converted to the xylose derivative (D) by Mitsunobu inversion to the inverted ester derivative (C') and saponification. The Mitsunobu reaction can be carried out with a variety of alkylazodicarboxylates such as diethylazodicarboxylate, the diisopropyl derivative, and the like, together with a phosphine such as triphenylphosphine, tributylphosphine, and the like, with a carboxylic acid such as a nitrobenzoic acid derivative. Mitsunobu reactions are described generally in Mitsunobu, O.; Yamada, Y. Bull. Chem. Soc. Japan 1967, 40, 2380-2382, The Use of Diethyl Azodicarboxylate and Triphenylphosphine in Synthesis and Transformation of Natural Products Mitsunobu, O. Synthesis 1981, 1-28, Castro, B. R. Org. React. 1983, 29, 1, Hughes, D. L. Org. React. 1992, 42, 335-656, Hughes, D. L. Org. Prep. 1996, 28, 127-164. (Review) each of which are hereby incorporated by reference in their entirety.

Preferred conditions use diisopropylazodicarboxylate, triphenyl- or tributylphosphine, 4-nitrobenzoic acid or 2,4-dinitrobenzoic acid or 3,5-dinitrobenzoic acid. More preferred conditions use diisopropylazodicarboxylate, triphenylphosphine, and 4-nitrobenzoic acid. The preferred solvent for the reaction is THF. The temperature of the reaction can range from room temperature to reflux. The preferred temperature is mixture of the reaction components at 40° C. followed by heating to 60° C. Purification can be accomplished by crystallization of C' from an appropriate alcohol solvent, with or without a non-polar solvent. Preferred solvents include isopropanol or ethanol with or without heptane, or methanol. More preferred conditions are crystallization from methanol. Saponification of the intermediate ester (C') to the xylose derivative (D) can be accomplished in an alcohol solvent and a solution of an alkali metal base, at temperature ranging from room temperature reflux. Preferred conditions for this reaction are an alcohol such as methanol or isopropanol with sodium- or potassium hydroxide. More preferred conditions are methanol and sodium hydroxide at room temperature. After aqueous workup the xylose derivative (D) can be purified by crystallization from a nonpolar solvent or can be used without purification.

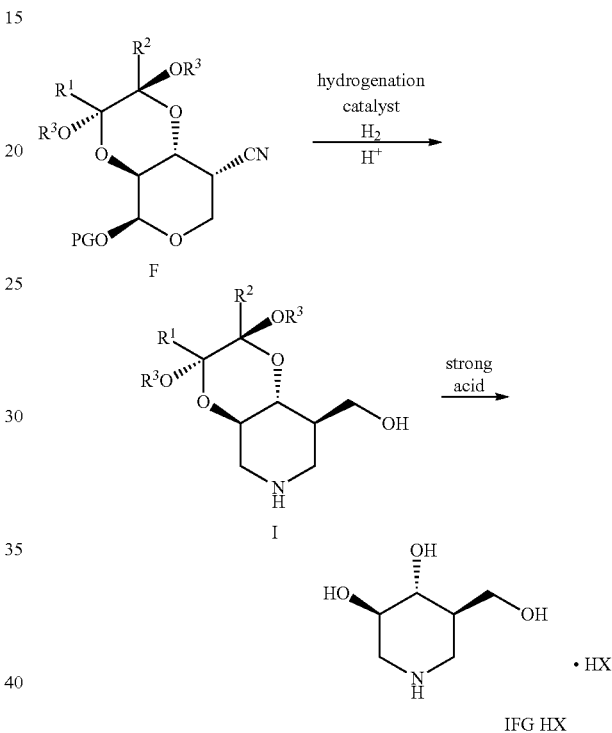

Conversion of a nitrile of the general formula (F) to protected isofagomine acid salt of the general formula (IFG HX) can be carried out in one step by proper choice of the protecting group at the anomeric center (e.g. benzyl or 4-methoxybenzyl). Nitrile reduction, deprotection at the anomeric center, ring closure, and hydrogenation of the cyclic imine can be accomplished in a single step under hydrogenation conditions to provide isofagomine acid salt in high yield. Catalytic hydrogenation can be carried out with a variety of catalysts including Pd/C, Pd(OH)$_2$/C, PtO$_2$, Pd(OAc)$_2$ or a combination of catalysts at loadings of about 1% to about 20%, under hydrogen gas pressure ranging from about 14 psi to about 100 psi, in protic or aprotic polar solvents, preferably an alcohol such as methanol, ethanol, isopropanol, with or without water co-solvent. Esters such as isopropyl acetate, ethyl acetate or methyl acetate can serve as aprotic solvents. The hydrogenation can be carried out in the presence of a mineral acid such as HCl, HBr, HClO$_4$, H$_3$PO$_4$, H$_2$SO$_4$, or a carboxylic acid such as tartaric acid or acetic acid. Acetic acid can serve as the solvent as well, with or without water as the co-solvent. The diketal protecting group is usually stable to many acids, allowing hydrogenation while keeping the protecting group intact. The hydrogenation can be run for short or extended periods of time as dictated by the rate of conversion. Preferred conditions use Pd(OH)$_2$/C with loadings of about 5% to about 20% under pressures from about 40 psi to about 100 psi in an alcoholic solvent and water with HCl, acetic acid, or tartaric acid. More preferred conditions are 20% loading Pd(OH)$_2$/C under 80 psi hydrogen gas in isopropanol and water with HCl or acetic acid. The protected isofagomine can be purified or deprotected without purification.

The isofagomine derivative of the general formula (I) can be converted into isofagomine by the action of a protic acid in water or an aqueous co-solvent system. Acids may include trifluoroacetic acid, trifluoromethanesulfonic acid, and the like. The reaction may be carried out in water at room temperature for about 2 to about 24 h. Solvent removal under reduced pressure has the advantage of evaporating volatile acids and volatile diones that are removed during the deprotection step. The resulting IFG can be isolated as a free base form or an acid salt.

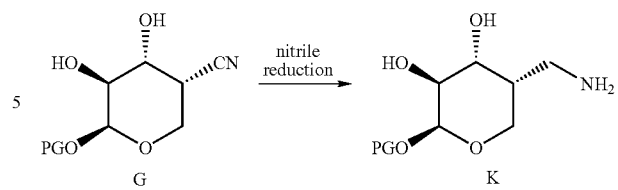

A compound of the general formula (K) can be accessed by reduction of the nitrile in a compound of the general formula (G). The reduction can be accomplished by hydrogenation using a metal catalyst and hydrogen in the presence of ammonia. Conditions include Raney nickel and hydrogen gas at pressures of about 14 psi to about 100 psi, in an alcohol with or without water. Preferred conditions are Raney nickel and hydrogen at 50 psi in methanol and water. The reduction can also be accomplished using a metal hydride. Conditions include reagents such as lithium aluminum hydride.

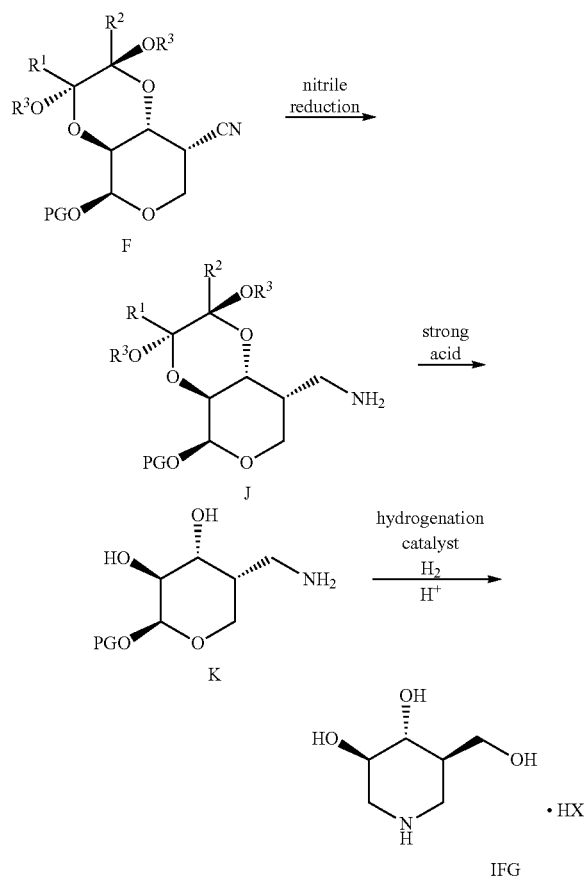

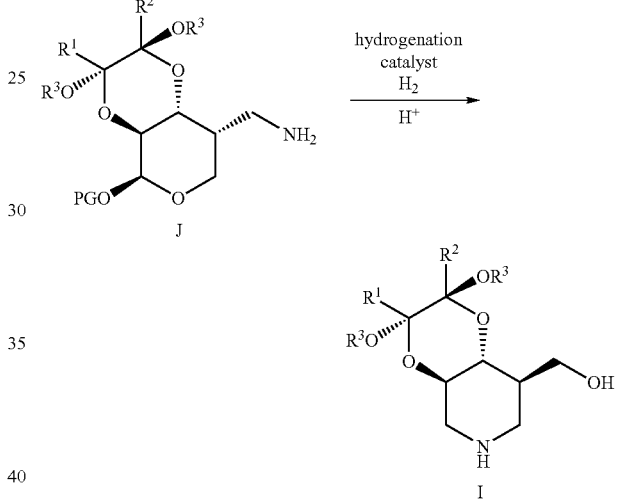

Two of the steps outlined previously can be reversed so that a compound of general formula (J) can be hydrogenated using the conditions set out in this application to provide a compound of the general formula (I). This product can be readily converted into IFG, IFG acid salt like IFG Tartrate.

Conversion to isofagomine tartrate can be accomplished via generation of the free base, purification on solid support, addition of tartaric acid, and crystallization of the product. The free base can be converted to the tartrate salt without purification on solid support. The free base can be formed by addition of a base such as a mineral base, ammonia gas or liquid, ammonium hydroxide solutions, or by exposing the salt to basic resin. Solid supports include silica gel, neutral or basic alumina at various activity grades, or a column of basic resin. Elution can be done with polar or non-polar solvents to provide the free isofagomine in a purified form. Conversion to the tartaric acid salt can be done with a range of acid to base ratios. Since tartaric acid is a diacid, the tartrate can be formed using 0.5 molar equivalents up to 1 molar equivalent of tartaric relative to isofagomine free base. Tartaric acid can be racemic (the D or -L form) or one of three stereoisomeric the L-(+) form, the D-(−) form, and the meso form. Preferred conditions for making the tartrate salt use ammonium hydroxide solution to generate the free base, 9:1 ethanol/ammonium hydroxide to elute the free base on a silica gel A compound of the general formula (F) can be reduced to the corresponding primary amine (J) by, for example, the action of hydride such as lithium aluminum hydride, selectride, borane, and the like, or by catalytic hydrogenation in the presence of an amine. Such conditions include Pd/C in the presence of triethylamine or Hunig's base.

Deprotection of (J) to the diol of general formula (K) can be accomplished using conditions previously set out in this application or known in the art.

A compound of the general formula (K) can be converted to IFG by catalytic hydrogenation using the conditions set out in this application. IFG can be further converted to IFG Tartrate, also using the conditions set out in this application for either direct conversion or purification on solid support followed by conversion to IFG Tartrate.

column, evaporation of solvent and excess ammonium hydroxide, formation of the tartrate salt in water/ethanol, and crystallization from water/ethanol.

IFG and tartaric acid can be combined over a range of stoichiometries. Since tartaric acid is a diacid, molar ratios of 2:1 to 1:1 IFG/tartaric acid provide stable salts. The preferred ratio is 1:1. The stoichiometry range is applicable to all isomers of tartaric acid.

Synthesis of IFG and its Derivatives Using a Ketal Intermediate

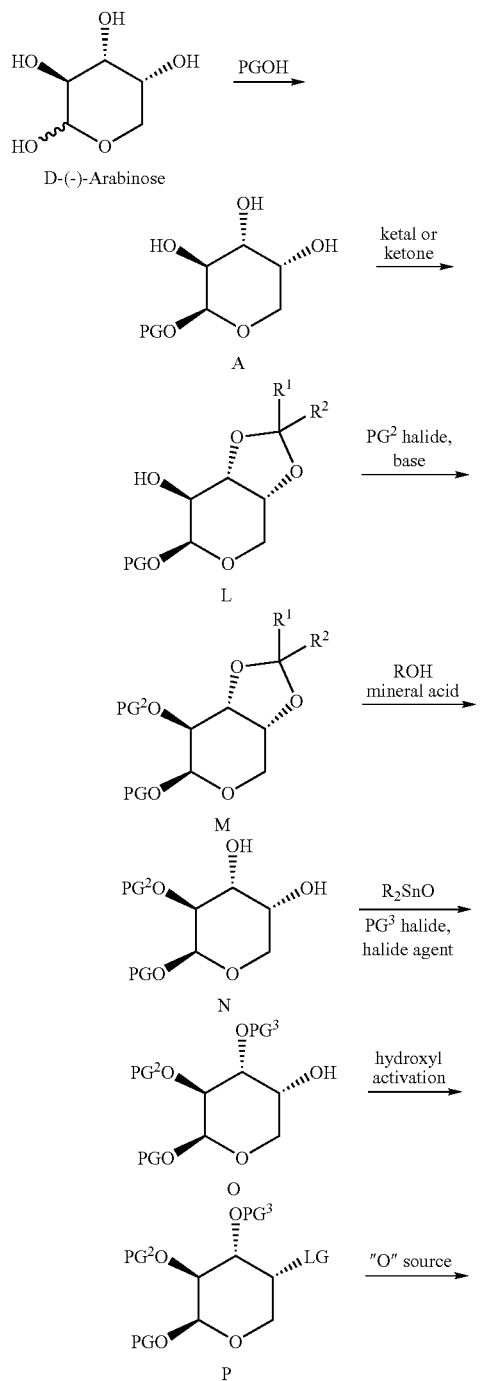

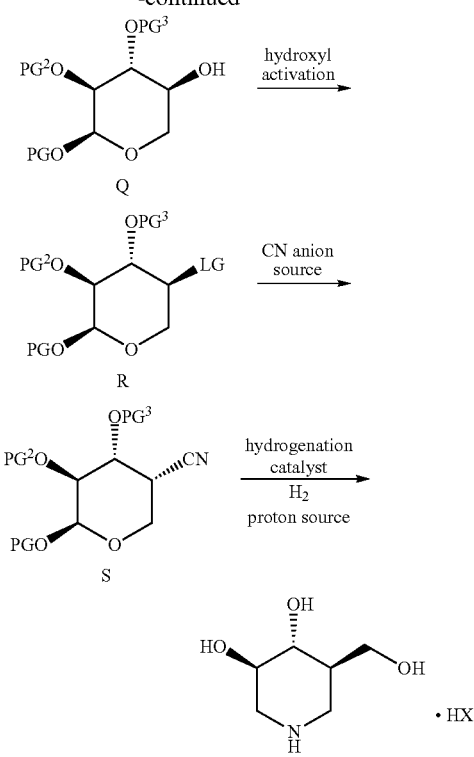

D-Arabinose can be converted to the corresponding protected glycoside (A) using an appropriate alcohol with or without solvent (neat reaction), and an activating agent. For instance the range of alcohols can include benzyl alcohol, or substituted benzyl alcohols such as methoxybenzyl alcohol, chlorobenzyl alcohol, methanol, ethanol, isopropanol, cyclohexylmethyl alcohol and the like in a solvent. Suitable solvents include, but are not limited to, methylene chloride, chloroform, THF, dioxane, DMF, DMA, or NMP, with an activating agent such as HCl, HBr, $H_2SO_4$, or some other mineral acid, or acetyl chloride, propionyl chloride, or another acid chloride of a carboxylic acid. The reaction can be run at temperatures ranging from about ambient temperature to about 100° C., for times ranging from about 2 to about 48 h. In one embodiment, the preferred alcohols are benzyl or substituted benzyl alcohols, and more preferred is benzyl alcohol. Preferred solvents include dioxane, THF or neat reaction, and more preferred is neat reaction. Preferred activating agents include acetyl chloride and $H_2SO_4$, and more preferred is acetyl chloride. Pure product can be readily isolated by precipitation with a non-polar solvent. The preferred solvent and temperature for this product is methyl-t-butyl ether at ambient temperature.

The obtained glycoside of general formula A can be further protected as an acetonide at the 3- and 4-hydroxyl groups by conversion of (A) to ketal (L) with a ketone or a dimethylketal, or enolether thereof, in the presence of an acid, with or without (neat) a polar co-solvent. For instance, aliphatic or aromatic ketones such as acetone, 2-butanone, benzophenone, cyclohexanone, or acetophenone, or their corresponding dialkylketals, can react with a vicinal diol in the presence of an acid such as $H_2SO_4$, p-toluenesulfonic acid, camphorsulfonic acid, or trimethylsilyltriflate. Co-solvents include methylene chloride, DMSO, DMF, DMA, and NMP. In some cases the ketone can also be the solvent, such as acetone. Reaction temperatures can range from about ambient temperature to about 100° C. For this reaction, the preferred conditions are acetone and 2,2-dimethoxypropane with p-toluenesulfonic acid at 40° C. Pure product can readily isolated by crystallization with a two component system including a polar and a non-polar component. Preferred conditions for this purification are ethyl acetate and heptane.

The acetonide (L) can be further protected as an ether at the 2-hydroxyl group by conversion to the corresponding alkoxide followed by subsequent reaction with an alkylating agent to provide a compound of general formula M. Previously reported protection utilized more expensive benzyl bromide and costly silver oxide. Formation of the alkoxide is readily accomplished with a strong base such as and alkali hydride in a polar aprotic solvent such as dialkyl ethers or THF, DMF, DMA, NMP, or DMSO corresponding to $PG^2$. $PG^2$ Alkylating agents include benzyl halide or substituted benzyl halides. Reaction temperatures can range from −20° C. to 20° C. For this reaction the preferred conditions are sodium hydride in DMF to generate the alkoxide at 0° C. to 10° C., followed by alkylation by benzyl chloride. Pure product can be readily isolated by precipitation with water and a non-polar wash to remove excess water. The preferred non-polar solvent for this purification is heptane.

Removal of the acetonide in the compound of general formula (M) to provide a diol of general formula (N) is accomplished with a dilute mineral acid such as HCl, HBr, $H_2SO_4$ in an alcohol such as methanol, ethanol, isopropanol, at ambient temperature. For this reaction, the preferred conditions are HCl in methanol at ambient temperature. Pure product (N) can be readily isolated by precipitation with water and a non-polar wash to remove excess water. The preferred non-polar solvent for this purification is heptane.

Additional protection of the diol is required for modification to the target molecule. Selective etherification to a molecule of the general formula (O) can be accomplished using a tin directed approach in a water-azeotroping solvent at reflux temperatures followed by etherification at moderate temperatures. Tin ethers can be formed using dialkyl or aryl tin(IV) oxides such as diphenyl, dimethyl, dibutyl, diisobutyl, or dioctyltin oxide in aprotic solvents such as benzene, toluene, or xylene. Subsequent alkylation can be accomplished with alkyl or alkylaryl halides such as benzyl bromide or benzyl chloride. The reaction can be accelerated through the use of agents such as CsF or tetraethylammonium chloride, and reaction temperatures can range from about ambient temperature to about 100° C. For this invention the preferred method uses dibutyltin oxide in toluene and benzyl chloride in the presence of tetrabutylammonium chloride. Purification can be readily accomplished by precipitation of the tin reagent with water. Final product can be obtained by crystallization from a two solvent system. The preferred crystallization solvents for this reaction are ethanol and heptane.

The triprotected intermediate arabinose derivative can be directly converted to the corresponding xylose derivative (Q) through an activated system (P). The involves activation of the arabinose hydroxyl to a discreet, isolable activated system (Q) followed by displacement with inversion using an inexpensive oxygen source. Activation can be with esters such as p-toluenesulfonate, methanesulfonate, trifluoromethanesulfonate, an the like, formed from the corresponding anhydride or sulfonyl chloride in the presence of an organic base such as pyridine, collidine, Hunig's base, triethylamine, in a non-polar solvent such as methylene chloride, chloroform, or toluene at temperatures from about −20° C. to about ambient temperature. Displacement with inversion of configuration can be accomplished with oxygen nucleophiles, preferably alkali or earth alkali metal nitrite in solvents commonly used for this type of reaction, e.g., methylene chloride, acetone, THF, DMF, DMA, NMP, and the like at temperatures from about 0° C. to about 40° C. Preferred conditions use trifluoromethanesulfonic anhydride and pyridine in methylene chloride at −10° C. followed by isolation of the triflate without the need for purification. Preferred conditions for displacement of the triflate are sodium or potassium nitrites in DMF at ambient temperature. Purified product can be readily obtained by crystallization from a two solvent system using a polar and a non-polar component. The preferred crystallization solvents for this reaction are isopropanol and heptane.

The triprotected xylose derivative of general formula (R) can be converted into the nitrile (S) with inversion of configuration through an activated system. Similar to the method described above, the route involves activation of the xylose hydroxyl to a discreet, isolable activated system (R) followed by displacement by a cyano source. Activation can be done again with esters of alkyl or aryl sulfonates, preferably p-toluenesulfonate, methanesulfonate, trifluoromethanesulfonate, and the like, which were formed from the corresponding anhydride or sulfonyl chloride in the presence of a mild organic base, such as pyridine, collidine, Hunig's base, triethylamine, and the like in a non-polar solvent such as methylene chloride, chloroform, or toluene at temperatures from about −20° C. to about ambient temperature. Displacement with inversion of configuration can be accomplished preferably with reagents such as alkali or earth alkali metal cyanides, or tetraalkylammonium cyanides in polar, aprotic solvents such as THF, DMF, DMA, NMP, DMSO, and the like at temperatures from about 0° C. to about 40° C. Preferred conditions use trifluoromethanesulfonic anhydride and pyridine in methylene chloride at −10° C. Preferred conditions for displacement of the triflate are tetraethylammonium cyanide in THF at ambient temperature. Purified product can be obtained by extraction followed by crystallization from an alcoholic solvent. The preferred solvent is ethanol.

Conversion of the nitrile intermediate to isofagomine hydrochloride can be carried out in one step depending on the choice of protecting groups. Nitrile reduction, triple deprotection, ring closure, and hydrogenation of the cyclic imine can be accomplished in a single step under hydrogenation conditions to provide isofagomine in high yield. Catalytic hydrogenation can be carried out with a variety of common catalysts used for such hydrogenation including Pd/C, $Pd(OH)_2$/C, $PtO_2$, $Pd(OAc)_2$ or a combination of catalysts at loadings of 1% to 20%, under hydrogen gas pressure ranging from about 14 psi to about 100 psi, in protic or aprotic polar solvents, preferably alcohols such as methanol, ethanol, isopropanol, or esters, or acetic acid. The hydrogenation is carried out in the presence of an acid such as HCl, HBr, $HClO_4$, $H_3PO_4$, $H_2SO_4$, acetic acid, trifluoroacetic acid, or tartaric acid. The hydrogenation can be run for short or extended periods of time with no risk of product decomposition. Preferred conditions are to run the reaction with a mixture of Pd/C and Pd(OH)2/C with loadings of about 5% to about 20% under pressures from about 40 psi to about 100 psi in an alcoholic solvent with HCl. More preferred conditions are 10% loading of Pd/C and 10% loading $Pd(OH)_2$/C under 80 psi hydrogen gas in ethanol with HCl. This hydrochloride salt can be converted to the isofagomine acid salt of the present invention.

Synthesis of IFG through L-Xylose

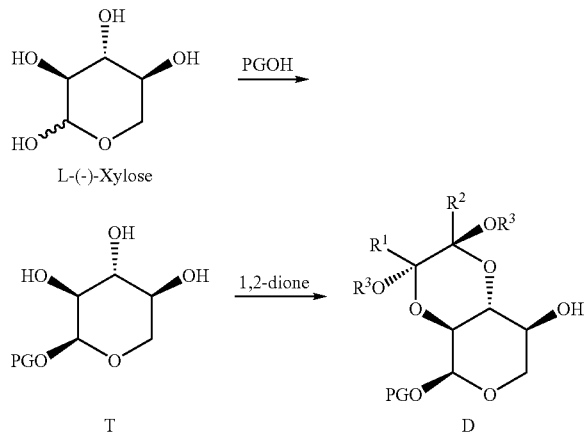

L-(−)-Xylose can also be used to make isofagomine. The sugar can be converted to the corresponding protected glycoside (T) using an appropriate alcohol with or without solvent (neat reaction), and an activating agent. For instance the range of alcohols can include benzyl alcohol, substituted benzyl alcohols such as methoxybenzyl alcohol, chlorobenzyl alcohol, diphenylmethanol, substituted diphenylmethanols, methanol, ethanol, isopropanol, cyclohexylmethyl alcohol and the like in a solvent such as methylene chloride, chloroform, THF, dioxane, DMF, DMA, or NMP, with an activating agent such as HCl, HBr, $H_2SO_4$, or some other mineral acid, or acetyl chloride, propionyl chloride, or another acid chloride of a carboxylic acid. The reaction can be run at temperatures ranging from ambient temperature to about 100° C., for times ranging from about 2 to about 48 h. For this invention the preferred alcohols are benzyl or substituted benzyl alcohols, and more preferred is benzyl alcohol. Preferred solvents include dioxane, THF or neat reaction, and more preferred is neat reaction. Preferred activating agents include acetyl chloride and $H_2SO_4$, and more preferred is acetyl chloride. Pure product can be readily isolated by precipitation with a nonpolar solvent. The preferred solvent and temperature for this product is methyl-t-butyl ether at ambient temperature.

The glycoside (T) can be taken directly to diketal (D) by reaction with a 1,2 dione or the dialkylketal thereof in the presence of a protic acid or a Lewis acid and an alcohol that may also act as the solvent. For instance, aliphatic or aromatic diones such as 1,2-butanedione, 1,2-cyclohexanedione, 1,2-diphenylethanedione, or 9,10-phenanthrenequinone, or their corresponding ketals, react with a vicinal diol in the presence of a protic acid such as HCl, $H_2SO_4$, camphorsulfonic acid, p-toluenesulfonic acid, or a Lewis acid such as boron trifluoride etherate or titanium tetrachloride. Alcohols include simple aliphatic alcohols such as methanol, ethanol, isopropanol, and the like at temperatures ranging from about 0° C. to reflux. Preferred conditions for this reaction are 1,2-butanedione or 1,2-cyclohexanedione, in methanol at ambient temperature to 35° C., with camphorsulfonic acid or boron trifluoride etherate. More preferred conditions are 1,2-butanedione in methanol at ambient temperature with camphorsulfonic acid. Pure product is readily obtained by crystallization.

Synthesis of Specific Tartrate Salts of IFG

In yet another embodiment, the invention provides a method for preparing the L-(+) tartaric acid salt of isofagomine. In one embodiment a method is provided to prepare the L-(+) tartaric acid salt of isofagomine represented by the structure:

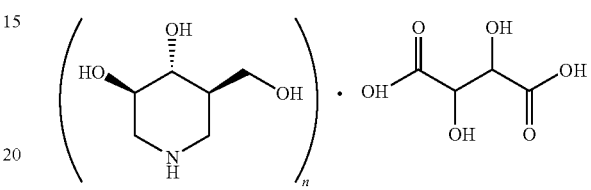

wherein n is 1 or 2. In one embodiment, n is 1.

L-(+) tartaric acid salt of isofagomine can be prepared using any one of the methods disclosed in the application (e.g. starting with D-(−)-arabinose or L-(−) xylose through a diketal intermediate as described supra). The L-(+) tartaric acid salt of isofagomine. wherein n=1 or 2 can then be prepared and isolated based on, for example, the disclosure set forth throughout U.S. Pat. No. 7,501,439, which is hereby incorporated by reference in its entirety, particularly Examples 1-3 from column 19, line 37-col. 24, line 10.

EXAMPLES

The present invention is further described by means of the examples, presented below. The use of such examples is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

Example 1

Synthesis of IFG Tartrate Through Dioxane-Fused Arabinose

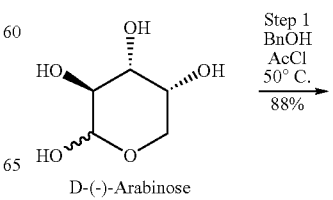

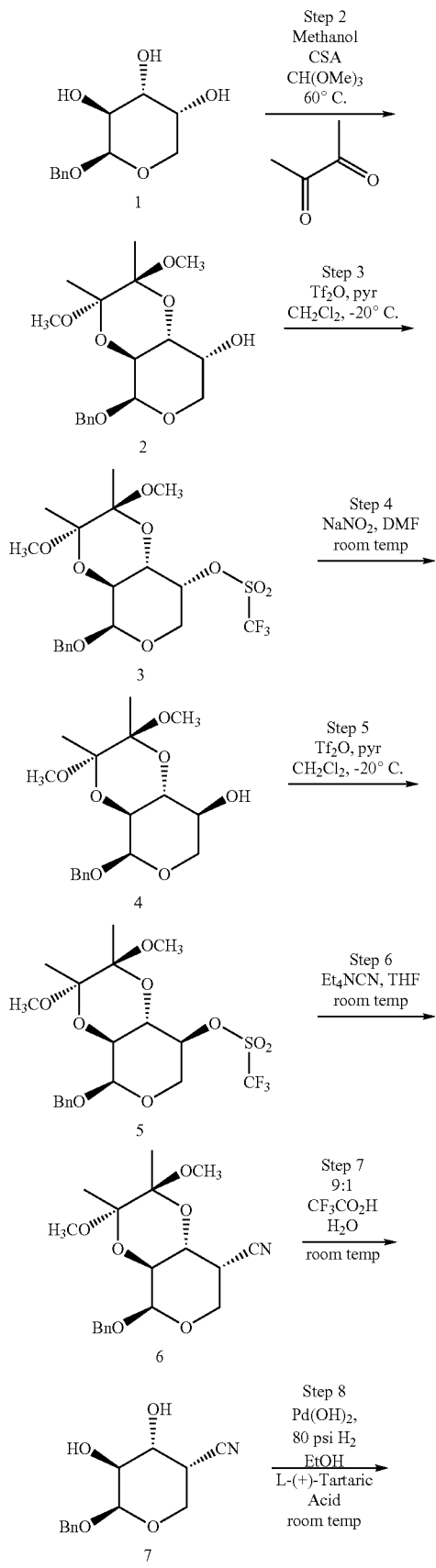

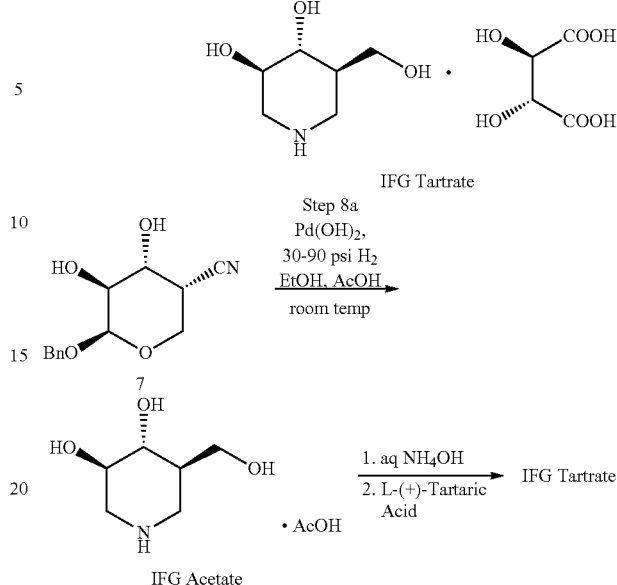

Step 1:

D-arabinose (250 g, 1.67 mol) and benzyl alcohol (606 mL, 5.83 mol) were stirred at 20° C. under nitrogen. Acetyl chloride (50 mL, 0.7 mol) was added at such a rate that the reaction temperature remained at 20-30° C. The reaction was heated to 50° C. for 16 h and reaction was monitored by TLC. The batch was cooled to 20° C. and diluted with MTBE (600 mL). The batch was further cooled to 0° C. for 3 h then filtered. The solid was washed with 3×300 mL MTBE and dried under vacuum. The product (1) was obtained as a white solid (349 g, 87%). $^1$H NMR (300 MHz, DMSO-d$_6$): δ 7.32 (m, 5H), 4.76 (s, 1H), 4.66 (d, J=12 Hz, 1H), 4.59 (m, 3H), 4.45 (d, J=12 Hz, 1H), 3.70 (m, 4H), 3.47 (dd, J=12, 3 Hz, 1H).

Step 2:

Benzyl arabinose (1, 225 g, 0.94 mol), 2,3-butanedione (90 mL, 1.03 mol), trimethylorthoformate (338 mL, 3.09 mol), and camphor-10-sulfonic acid (β) (10.3 g, 47 mol) were mixed in methanol (1 L) under nitrogen at 20° C. The mixture was heated to 60° C. and monitored by TLC until the reaction was complete, typically 16 hours (SiO$_2$ plates, 5% methanol in dichloromethane for the starting material, 35% ethyl acetate in hexanes for the product). The reaction was quenched by adding triethylamine (20 mL) at 50° C. then cooling to room temperature. Solvent was evaporated and the product (2) was crystallized from isopropanol (45%). m.p. 147-148° C. $^1$H NMR (300 MHz, CDCl$_3$): δ 7.32 (m, 5H), 4.95 (d, J=3 Hz, 1H), 4.75 (d, J=12 Hz, 1H), 4.68 (d, J=12 Hz, 1H), 4.16 (m, 2H), 3.93 (s, 1H), 3.81 (d, J=12 Hz, 1H), 3.70 (d, J=12 Hz, 1H), 3.27 (s, 3H), 3.22 (s, 3H), 2.62 (s, 1H), 1.33 (s, 3H), 1.31 (s, 3H).

Step 3:

(2S,3S,4aS,5R,8R,8aR)-5-(benzyloxy)-2,3-dimethoxy-2,3-dimethylhexahydro-2H-pyrano[4,3-b][1,4]dioxin-8-ol (2, 150 g, 0.423 mol) and pyridine (137 mL, 1.7 mol) were mixed in methylene chloride (1.5 L) under nitrogen at room temperature. The solution was cooled to −20° C. and trifluoromethanesulfonic anhydride (114 mL, 0.68 mol) was added dropwise such that the temperature did not exceed −5° C. The mixture was stirred at −20° C. for one hour, then excess reagent was quenched with 2 N HCl (500 mL). The solution was further washed with saturated sodium bicarbonate (800 mL), water (800 mL), and brine (500 mL). N,N-Diisopropylethylamine (15 mL) was added to the organic phase. The combined organics were dried MgSO₄, filtered, and evaporated to dryness at 20-30° C. The product (3) was used without further purification. ¹H NMR (300 MHz, CDCl₃): δ 7.33 (m, 5H), 4.99 (m, 2H), 4.72 (s, 2H), 4.25 (dd, J=12, 3 Hz, 1H), 4.08 (dd, J=11, 3 Hz, 1H), 3.91 (d, J=14 Hz, 1H), 3.79 (d, J=14 Hz, 1H), 3.26 (s, 3H), 3.22 (s, 3H), 1.32 (s, 3H), 1.27 (s, 3H).

Step 4:

(2S,3S,4aS,5R,8R,8aS)-5-(benzyloxy)-2,3-dimethoxy-2,3-dimethylhexahydro-2H-pyrano[4,3-b][1,4]dioxin-8-yl trifluoromethanesulfonate (3) from the previous step was taken up in DMF under nitrogen and cooled to 15° C. Potassium nitrite was added in one portion and the mixture was agitated at 30-35° C. The mixture was filtered, then solvent was evaporated with a solution temperature at 30-40° C. The residue was chromatographed on silica gel using 30% ethyl acetate in hexanes. The product (4) was obtained as a solid (105.6 g, 70%). m.p. 51-52° C. ¹H NMR (300 MHz, CDCl₃): δ 7.31 (m, 5H), 4.86 (d, J=4, 1H), 4.76 (d, J=13 Hz, 1H), 4.66 (d, J=13 Hz, 1H), 4.03 (t, J=10 Hz, 1H), 3.85 (m, 1H), 3.68 (m, 1H), 3.56 (t, J=10 Hz, 1H), 3.30 (s, 3H), 3.23 (s, 3H), 2.25 (m, 1H), 1.34 (s, 3H), 1.32 (s, 3H).

Step 5:

(2S,3S,4aS,5R,8S,8aR)-5-(benzyloxy)-2,3-dimethoxy-2,3-dimethylhexahydro-2H-pyrano[4,3-b][1,4]dioxin-8-ol (4, 105 g, 0.3 mol) and pyridine (96 mL, 1.2 mol) were mixed in methylene chloride (1 L) under nitrogen at room temperature. The solution was cooled to −20° C. and trifluoromethanesulfonic anhydride (80 mL, 0.47 mol) was added dropwise such that the temperature did not exceed −5° C. The mixture was stirred at −20° C. for one hour, then excess reagent was quenched with 2 N HCl (350 mL). The solution was further washed with saturated sodium bicarbonate (500 mL), water (500 mL), and brine (500 mL). N,N-diisopropylethylamine (10 mL) was added to the organic phase. The combined organics were dried MgSO₄, filtered, and evaporated to dryness at 20-30° C. The product (5) was used without further purification.

Step 6:

(2S,3S,4aS,5R,8S,8aS)-5-(benzyloxy)-2,3-dimethoxy-2,3-dimethylhexahydro-2H-pyrano[4,3-b][1,4]dioxin-8-yl trifluoromethanesulfonate (5) from the previous step was mixed with dry THF (700 mL) under nitrogen. Tetraethylammonium cyanide (50.1 g, 0.32 mol) was added as one portion and the mixture was heated to 35° C. for 16 h. The reaction was cooled to room temperature and diluted with ethyl acetate (700 mL). The organic phase was washed with brine (2×500 mL). The combined aqueous washes were washed with ethyl acetate (700 mL). The organic phases were combined and dried with MgSO₄. The organic phase was filtered and evaporated to dryness. The crude mixture (121 g) was dissolved in isopropanol (450 mL) at 50° C., then cooled to room temperature with stirring. The solution was cooled to 5° C. for 16 h. Solid was filtered and washed with heptane (2×100 mL). The solid was dissolved in isopropanol (420 mL) at 60° C. and heptane (120 mL) was added slowly while the temperature was kept at 50-60° C. The solution was cooled to room temperature with stirring for 16 h. The solid (6) was obtained by filtration, washed with heptane (100 mL), and dried under vacuum (60.65 g, 62%). m.p. 121-122° C. ¹H NMR (300 MHz, CDCl₃): δ 7.34 (m, 5H), 4.97 (d, J=3 Hz, 1H), 4.71 (s, 2H), 4.21 (dd, J=12, 5 Hz, 1H), 4.03 (dd, J=9, 4 Hz, 1H), 3.90 (dd, J=12, 2 Hz, 1H), 3.79 (dd, J=12, 1 Hz, 1H), 3.26 (s, 3H), 3.25 (s, 3H), 2.99 (m, 1H), 1.33 (s, 3H), 1.32 (s, 3H).

Step 7:

(2S,3S,4aS,5S,8R,8aR)-5-(benzyloxy)-2,3-dimethoxy-2,3-dimethylhexahydro-2H-pyrano[4,3-b][1,4]dioxine-8-carbonitrile (6, 20 g, 0.055 mol) was mixed with 9:1 trifluoroacetic acid/water (40 mL) at 20° C. under nitrogen and stirred for 16 h. The mixture was evaporated to dryness at 30-35° C. Heptane (50 mL) was added and the mixture was evaporated. The residue was mixed with heptane (50 mL) and stirred for 3 h. The solid product (7) was isolated by filtration, washed with heptane (2×100 mL), and dried under vacuum (13.6 g, 99%). m.p. 103-104° C. ¹H NMR (300 MHz, D₂O): δ 7.30 (m, 5H), 4.95 (d, J=4 Hz, 1H), 4.61 (d, J=12 Hz, 1H), 4.47 (d, J=12 Hz, 1H), 3.94 (dd, J=10, 5 Hz, 1H), 3.87 (dd, J=12, 2 Hz, 1H), 3.73 (dd, J=12, 2 Hz, 1H), 3.65 (dd, J=10, 4 Hz, 1H), 3.29 (m, 1H).

Step 8:

(3R,4R,5S,6S)-6-(benzyloxy)-4,5-dihydroxytetrahydro-2H-pyran-3-carbonitrile (7, 1.0 g, 0.004 mol) was mixed with ethanol (30 mL), heated to 35° C., stirred with charcoal, and filtered. The solution was mixed with water (8 mL), and L-(+)-tartaric acid (0.662 g, 4.4 mmol), and Degussa Type E101 NE/W (20% Pd(OH)₂ on carbon) (0.4 g). The mixture was stirred under hydrogen gas (80 psi) at 30° C. for 24 h. The mixture was diluted with water (10 mL) and filtered through diatomaceous earth. Solvent was removed under reduced pressure. The residue was dissolved in water (15 mL) and washed with dichloromethane (2×10 mL). The aqueous phase was stirred with charcoal 0.6 g), metal scavenging agent (0.3 g), alumina (0.3 g), and florisil (0.3 g) for 16 h at ambient temperature. The mixture was filtered and ethanol (75 mL) was added dropwise over 1 h. The mixture was cooled to 0° C. for 3 h and filtered. The solid was washed with ethanol (30 mL). The solid was dried under vacuum and IFG tartrate was obtained as a white solid (0.578 g, 48%).

Alternative Step 8:

Step 8a: (3R,4R,5S,6S)-6-(benzyloxy)-4,5-dihydroxytetrahydro-2H-pyran-3-carbonitrile (7, 1.2 g, 0.005 mol) was mixed with ethanol (80 mL), acetic acid (0.025 mL), and Degussa Type E101 NE/W (20% Pd(OH)₂ on carbon) (0.6 g), and stirred under hydrogen gas (60 psi) at 20° C. for 16 h. The mixture was filtered (diatomaceous earth) and evaporated to dryness. Chromatography on silica gel with 9:1 ethanol/29% aq NH₄OH yielded the product as a free base. The solvent was evaporated; product was dissolved in ethanol (6 mL) and stirred. L-Tartaric acid (0.429 g) was dissolved in ethanol (11 mL) and added in one portion at 45° C. The batch was cooled to room temperature and stirred for 1 h. IFG tartrate was filtered and washed with cold ethanol, then dried under vacuum (0.348 g, 24%).

Reversal of the steps 7 and 8 also is possible:

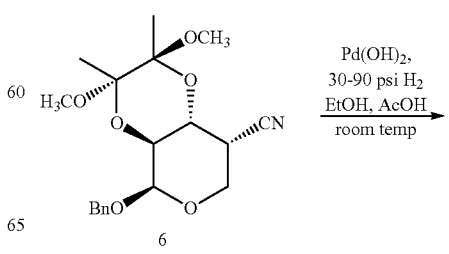

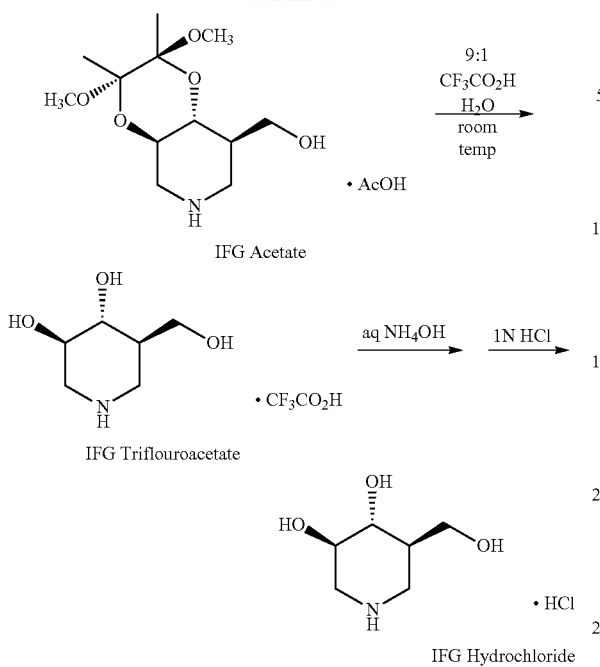

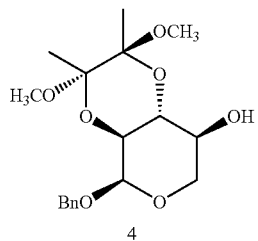

Steps 8, then 7:

(2S,3S,4aS,5S,8R,8aR)-5-(benzyloxy)-2,3-dimethoxy-2,3-dimethylhexahydro-2H-pyrano[4,3-b][1,4]dioxine-8-carbonitrile (6, 2.0 g, 0.002 mol) was mixed with methanol (100 mL), acetic acid (0.025 mL), and Degussa Type E101 NE/W (20% Pd(OH)$_2$ on carbon) (0.985 g), and stirred under hydrogen gas (60 psi) at 20° C. for 72 h. The reaction was filtered (diatomaceous earth) and evaporated to dryness. The residue (IFG Acetate) was mixed with 9:1 trifluoroacetic acid/water (5 mL) at 20° C. under nitrogen and stirred for 4 h. The mixture was evaporated to dryness at 30-35° C. The residue (IFG Trifluoroacetate) was chromatographed on silica gel with 70:30:5 methylene chloride/methanol/29% aq NH$_4$OH. The product was isolated by evaporation, dissolved in 1 N HCl (5 mL), and lyophilized to yield IFG Hydrochloride. m.p. 128-129° C. The conversion to the tartrate salt is described in this application.

Alternative method from 2 to 4: (2S,3S,4aS,5R,8R,8aR)-5-(benzyloxy)-2,3-dimethoxy-2,3-dimethylhexahydro-2H-pyrano[4,3-b][1,4]dioxin-8-ol (2, 8 g, 0.023 mol), triphenylphosphine (11.84 g, 0.045 mol), and 4-nitrobenzoic acid (7.54 g, 0.045 mol) were mixed in THF (80 mL) under nitrogen and heated to 40° C. Diisopropylazodicarboxylate (9.13 g, 0.045 mol) was added dropwise, then the mixture was heated to 62° C. for 17 h. The reaction was cooled to room temperature, solvent was evaporated, and the product (8) was crystallized from methanol (86%). m.p. 170-171° C. $^1$H NMR (300 MHz, CDCl$_3$): δ 8.21 (d, J=9 Hz, 2H), 8.10 (d, J=9 Hz, 2H), 7.37-7.19 (m, 5H), 5.14 (m, 1H), 4.85 (d, J=3.6 Hz, 1H), 4.71 (d, J=12.6 Hz, 1H), 4.61 (d, J=12.6 Hz, 1H), 4.31 (t, J=9.9 Hz, 1H), 3.89-3.77 (m, 2H), 3.58 (t, J=10.6 Hz, 1H), 3.39 (s, 3H), 3.21 (s, 3H), 1.28 (s, 3H), 1.19 (s, 3H).

(2S,3S,4aS,5R,8S,8aR)-5-(benzyloxy)-2,3-dimethoxy-2,3-dimethylhexahydro-2H-pyrano[4,3-b][1,4]dioxin-8-yl 4-nitrobenzoate (8, 6.7 g, 0.013 mol) was suspended in isopropanol (80 mL) at 20° C. A solution of 5N NaOH (5.4 mL) was added dropwise and stirred at 20° C. for 14 h. The reaction volume was reduced by two thirds, methylene chloride was added (80 mL) and the organic phase was washed water and 10% NaCl. The solvent was evaporated and the product was obtained as a foam (quantitative). The NMR was identical to compound 4 as reported in this application.

Example 2

Synthesis of IFG and IFG Tartrate Via a Ketal Intermediate

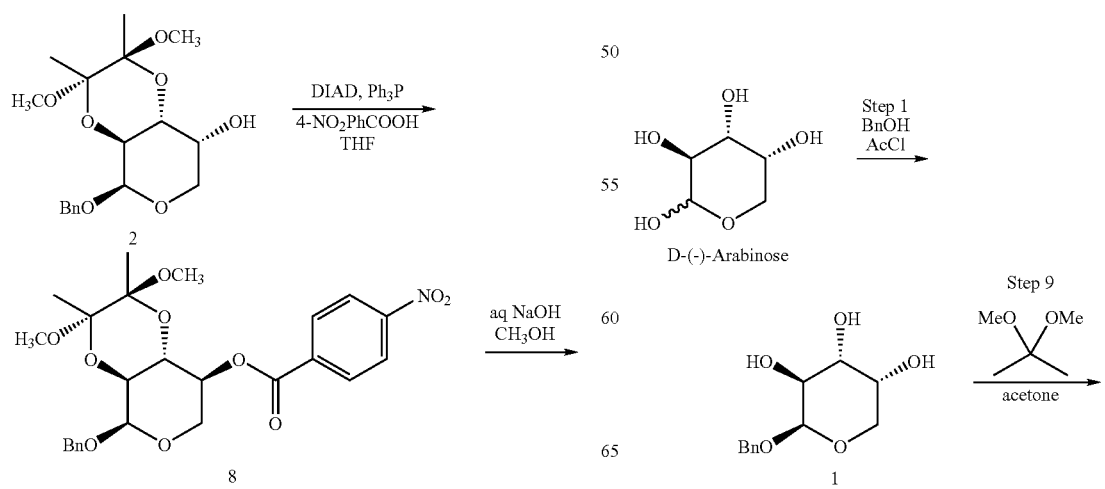

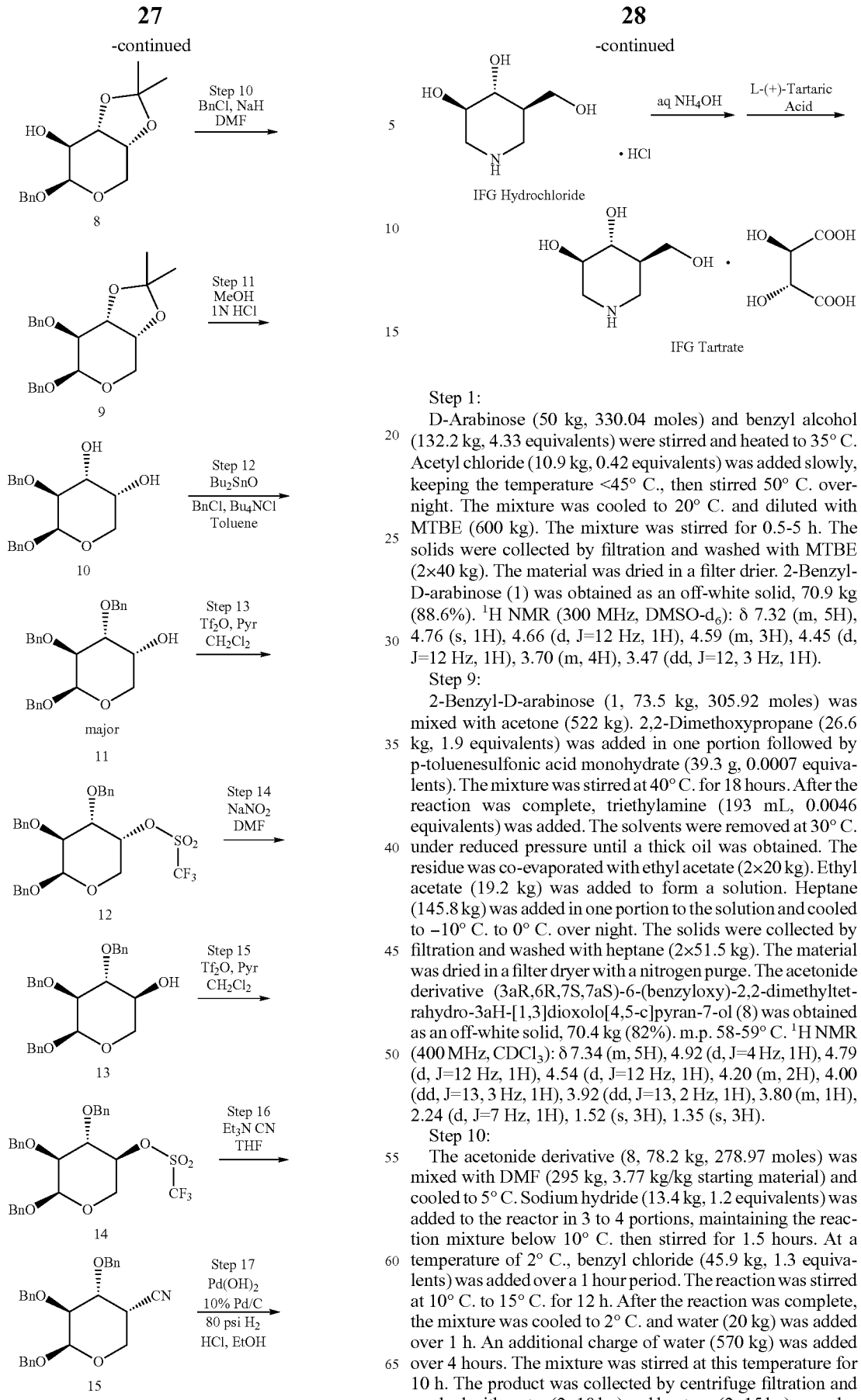

Step 1:

D-Arabinose (50 kg, 330.04 moles) and benzyl alcohol (132.2 kg, 4.33 equivalents) were stirred and heated to 35° C. Acetyl chloride (10.9 kg, 0.42 equivalents) was added slowly, keeping the temperature <45° C., then stirred 50° C. overnight. The mixture was cooled to 20° C. and diluted with MTBE (600 kg). The mixture was stirred for 0.5-5 h. The solids were collected by filtration and washed with MTBE (2×40 kg). The material was dried in a filter drier. 2-Benzyl-D-arabinose (1) was obtained as an off-white solid, 70.9 kg (88.6%). $^1$H NMR (300 MHz, DMSO-$d_6$): δ 7.32 (m, 5H), 4.76 (s, 1H), 4.66 (d, J=12 Hz, 1H), 4.59 (m, 3H), 4.45 (d, J=12 Hz, 1H), 3.70 (m, 4H), 3.47 (dd, J=12, 3 Hz, 1H).

Step 9:

2-Benzyl-D-arabinose (1, 73.5 kg, 305.92 moles) was mixed with acetone (522 kg). 2,2-Dimethoxypropane (26.6 kg, 1.9 equivalents) was added in one portion followed by p-toluenesulfonic acid monohydrate (39.3 g, 0.0007 equivalents). The mixture was stirred at 40° C. for 18 hours. After the reaction was complete, triethylamine (193 mL, 0.0046 equivalents) was added. The solvents were removed at 30° C. under reduced pressure until a thick oil was obtained. The residue was co-evaporated with ethyl acetate (2×20 kg). Ethyl acetate (19.2 kg) was added to form a solution. Heptane (145.8 kg) was added in one portion to the solution and cooled to −10° C. to 0° C. over night. The solids were collected by filtration and washed with heptane (2×51.5 kg). The material was dried in a filter dryer with a nitrogen purge. The acetonide derivative (3aR,6R,7S,7aS)-6-(benzyloxy)-2,2-dimethyltetrahydro-3aH-[1,3]dioxolo[4,5-c]pyran-7-ol (8) was obtained as an off-white solid, 70.4 kg (82%). m.p. 58-59° C. $^1$H NMR (400 MHz, CDCl$_3$): δ 7.34 (m, 5H), 4.92 (d, J=4 Hz, 1H), 4.79 (d, J=12 Hz, 1H), 4.54 (d, J=12 Hz, 1H), 4.20 (m, 2H), 4.00 (dd, J=13, 3 Hz, 1H), 3.92 (dd, J=13, 2 Hz, 1H), 3.80 (m, 1H), 2.24 (d, J=7 Hz, 1H), 1.52 (s, 3H), 1.35 (s, 3H).

Step 10:

The acetonide derivative (8, 78.2 kg, 278.97 moles) was mixed with DMF (295 kg, 3.77 kg/kg starting material) and cooled to 5° C. Sodium hydride (13.4 kg, 1.2 equivalents) was added to the reactor in 3 to 4 portions, maintaining the reaction mixture below 10° C. then stirred for 1.5 hours. At a temperature of 2° C., benzyl chloride (45.9 kg, 1.3 equivalents) was added over a 1 hour period. The reaction was stirred at 10° C. to 15° C. for 12 h. After the reaction was complete, the mixture was cooled to 2° C. and water (20 kg) was added over 1 h. An additional charge of water (570 kg) was added over 4 hours. The mixture was stirred at this temperature for 10 h. The product was collected by centrifuge filtration and washed with water (2×10 kg) and heptane (2×15 kg) spun dry overnight. The dibenzyl derivative (3aR,6R,7S,7aR)-6,7-bis(benzyloxy)-2,2-dimethyltetrahydro-3aH-[1,3]dioxolo[4,5-c]pyran (9) was obtained as a white solid, 74.0 kg (71.6%).

Step 11:

The dibenzyl derivative (9, 37.6 kg, 101.50 moles) was added to methanol, AR (259 kg, 8.7 kg/kg starting material) and the contents were cooled to 15° C. A 2.5 N HCl solution (76.2 kg, 1.8 equivalents) was added over 1 hour. Additional water (20 kg) was added and the mixture was stirred for 12 hours at 15° C. Water (1035 kg, 4× vol methanol, AR) was added to the reactor and stirred for at least 0.5 h. The product was filtered onto a centrifuge and washed with water (2×10 kg) and heptane (2×15 kg) and spun dry overnight. The diol (3R,4R,5S,6R)-5,6-bis(benzyloxy)tetrahydro-2H-pyran-3,4-diol (10) was obtained as a white solid, 31.5 kg (94%).

Step 12:

The diol derivative (10, 37.5 kg, 113.51 moles) was mixed with toluene (207.6 kg, 5.5 kg/kg of diol) and dibutyltinoxide (31.1 kg, 1.1 equivalents). The reactor was equipped with a Dean-Stark apparatus and the reactor contents were heated to reflux (approx. 110° C.) until water no longer collected for removal (8-12 h). The reactor contents were cooled to 35° C. and tetrabutylammonium chloride (18.3 kg, 0.5 equivalents) was added in one portion. Benzyl chloride (15.8 kg, 1.1 equivalents) was added at a rate that kept the temperature <40° C. and stirring continued at 35° C. for 12 h. The addition and 12 h stirring were repeated daily for 4 days until the reaction was complete. After the reaction was complete, the mixture was cooled to 25° C., water (150 kg) was added in one portion, and the contents were stirred overnight. The reaction mixture was filtered through a bed of Celite (1 kg/kg of diol) and the bed was rinsed with toluene (10 kg). The filtrate was allowed to settle (1 h) and the layers were separated. Water addition, stirring, filtration, and separation were repeated. The aqueous layers were combined and extracted with ethyl acetate (25 kg), and the layers were separated. The organic layers were combined and concentrated under vacuum at 45° C. to a minimum stirable volume. Heptane (102.6 kg) was added. The mixture was stirred for 20 minutes, cooled to 0° C., and stirred for 8-12 h. The solids were collected by filtration and washed with heptane (10 kg). Crude solids were dissolved in 6:1 heptane/200 pf ethanol (7 kg/kg crude solid) at 35° C., cooled to −5° C. to 0° C. and stirred overnight. The solids were collected by filtration and washed with heptane (10 kg). Typically, 2 or more re-crystallizations were required to remove the impurities. The purified tribenzyl derivative was dried in a vacuum oven at 30° C. (3R,4R,5S,6R)-4,5,6-Tris(benzyloxy)tetrahydro-2H-pyran-3-ol (11) was obtained as a white solid, 17.5 kg (37%). m.p. 59-60° C. $^1$H NMR (400 MHz, CDCl$_3$): δ 7.38 (m, 15H), 4.89 (d, J=4 Hz, 1H), 4.82 (d, J=12 Hz, 1H), 4.71 (m, 3H), 4.57 (d, J=12 Hz, 1H), 4.55 (d, J=12 Hz, 1H), 4.01 (br s, 1H), 3.95 (dd, J=10, 3 Hz, 1H), 3.83 (m, 2H), 3.71 (dd, J=12, 2 Hz, 1H), 2.56 (br s, 1H).

Step 13:

The tribenzylarabinose derivative (11, 12.0 kg, 28.54 moles) was mixed with methylene chloride (79.2 kg, 6.6 kg/kg starting material) and pyridine (11.3 kg, 5 equivalents) and cooled to −10° C. Trifluoromethanesulfonic anhydride (10.1 kg, 1.25 equivalents) was added at a rate that kept the temperature below 0° C. The reaction mixture was stirred at −10° C. to 0° C. until starting material was consumed. Once complete, the reaction mixture was washed with 7.5% HCl solution (3×68 kg, 17 equivalents) and water (48 kg). During the washes, the temperature of the reaction mixture was maintained at <5° C. The mixture was adjusted to pH≧6 by washing with 7.5% NaHCO$_3$ solution (55.0 kg). Triethylamine (0.4 kg, 0.3 kg/kg starting material) was added and the organic phase was dried with anhydrous K$_2$CO$_3$ (1.2 kg, 0.1 equivalents). The mixture was filtered and concentrated to dryness under vacuum at 20° C. to 35° C. to give (3S,4S,5S,6R)-4,5,6-Tris(benzyloxy)tetrahydro-2H-pyran-3-yl trifluoromethanesulfonate (12). The triflate was used without purification. $^1$H NMR (300 MHz, CDCl$_3$): δ 7.31-7.16 (m, 15H), 5.12 (br s, 1H), 4.83 (d, J=4 Hz, 1H), 4.76 (d, J=11 Hz, 1H), 4.64 (m, 2H), 4.50 (d, J=9 Hz, 1H), 4.46 (d, J=8 Hz, 1H), 3.97 (dd, J=10, 3 Hz, 1H), 3.86 (d, J=14 Hz, 1H), 3.77-3.72 (m, 2H).

Step 14:

The triflate (12) was dissolved in DMF (36.2 kg, 3.02 kg/kg starting material) and cooled to 10° C. Sodium nitrite (5.9 kg, 3.0 equivalents) was added, the solution exothermed to approximately 30° C., then the reaction mixture was cooled to 15° C. to 25° C. and stirred for 12-16 h. The mixture was cooled to 5° C., and water (152 kg, 4.2 kg/kg DMF) was added at a rate that kept the temperature <15° C. The resulting mixture was agitated at 10° C. for 2 hours. The solids were filtered and washed with water (2×12 kg). The filtered solids were dissolved in ethyl acetate (21.6 kg, 1.8 kg/kg starting material). The solution was washed with brine (15.5 kg), dried with MgSO$_4$ (2.5 kg), filtered, and the filtrate was concentrated to dryness under vacuum at 35° C. Isopropanol (9.5 kg) was added and heated to 75° C. to dissolve the crude product. Heptane (24.6 kg) was added to the solution and the mixture cooled to 15° C. to 25° C. The mixture was further cooled to 0° C. and stirred overnight. The solids were filtered and washed with heptane (2×8.2 kg). The material was dried in a vacuum oven. (3S,4R,5S,6R)-4,5,6-Tris(benzyloxy)tetrahydro-2H-pyran-3-ol (13) was obtained as a yellow solid, 5.3 kg (44%). $^1$H NMR (300 MHz, CDCl$_3$): δ 7.37 (m, 15H), 4.96 (d, J=11 Hz, 1H), 4.80 (m, 2H), 4.68 (d, J=12 Hz, 1H), 4.61 (m, 2H), 4.53 (d, J=12 Hz, 1H), 3.78 (m, 1H), 3.67 (m, 3H), 3.50 (dd, J=9, 3 Hz, 1H), 2.42 (br s, 1H).

Step 15:

The tribenzylxylose derivative (13, 10.4 kg, 24.73 moles) was mixed with methylene chloride (68.6 kg, 6.6 kg/kg starting material) and pyridine (9.8 kg, 5 equivalents) and cooled to −10° C. Trifluoromethanesulfonic anhydride (8.7 kg, 1.25 equivalents) was added at a rate that kept the temperature below 0° C. The reaction mixture was stirred at −10° C. to 0° C. until starting material was consumed. Once complete, the reaction mixture was washed with 7.5% HCl solution (3×58.9 kg, 17 equivalents) and water (41.6 kg). During the washes, the temperature of the reaction mixture was maintained at <5° C. The mixture was adjusted to pH≧6 by washing with saturated NaHCO$_3$ solution (44.6 kg). Triethylamine (0.4 kg, 0.3 kg/kg starting material) was added and the organic phase was dried with anhydrous K$_2$CO$_3$ (1.2 kg, 0.1 equivalents). The mixture was filtered and concentrated to dryness under vacuum at 20° C. to 35° C. to yield (3S,4S,5S,6R)-4,5,6-tris(benzyloxy)tetrahydro-2H-pyran-3-yl trifluoromethanesulfonate (14).

Step 16:

The triflate (14) was dissolved in THF (29 kg, 2.8 kg/kg starting material) and cooled to 10° C. Tetraethylammonium cyanide (4.6 kg, 1.2 equivalents) was added, the solution exothermed, then the reaction mixture was cooled to 20° C. and stirred for 12 h. Ethyl acetate (21.8 kg) was added and the organic phase was washed with 10% NaCl solution (3×14.3 kg). The combined aqueous layers were extracted with ethyl acetate (21.8 kg). The organic layers were combined, dried with MgSO$_4$ (2 kg), filtered, and concentrated to dryness under. Ethanol (200 pf, 3.23 kg/kg starting material) was added and heated to 70° C. to dissolve the crude product. The solution was cooled to 20° C., then further cooled to 5° C. and stirred overnight. The solids were filtered and washed with heptane (2×10.4 kg). Crystallization from 200 pf ethanol (7 mL/g solids) was repeated. The solids were filtered and washed with heptane (2×10.4 kg). The material was dried in a vacuum oven. (3R,4R,5S,6S)-4,5,6-Tris(benzyloxy)tetrahydro-2H-pyran-3-carbonitrile (15) was obtained as a light brown solid, 6.3 kg (59%). $^1$H NMR (300 MHz, CDCl$_3$): δ 7.31 (m, 15H), 4.90 (d, J=3 Hz, 1H), 4.81-4.73 (complex, 3H), 4.70 (d, J=12 Hz, 1H), 4.62 (d, J=12 Hz, 1H), 4.55 (d, J=12 Hz, 1H), 3.99 (dd, J=9, 5 Hz, 1H), 3.91 (dd, J=12, 3 Hz, 1H), 3.82-3.74 (overlapping signals, 2H), 3.13 m, 1H).

Step 17:

The nitrile derivative (15, 2.5 kg, 5.8 moles) was dissolved in absolute ethanol (138.1 kg) and heated at 35° C. until a clear solution was obtained. Moistened palladium on carbon was added (250 g; 10% w/w), followed by palladium hydroxide, (250 g; 20% w/w) and hydrochloric acid (0.6 L). The solution was purged twice with nitrogen and once with hydrogen. The solution was pressurized to 80 psi with hydrogen, stirred, and heated to 35° C. for 72 hours, repressurizing as necessary. The mixture was filtered and concentrated under vacuum at 30° C. to 35° C. Crude isofagomine hydrochloride was mixed with aq NH$_4$OH (3 L). The solution was filtered and purified on a silica gel column (approx 20 kg) using 9:1 EtOH/aq NH$_4$OH solvent system. The product was concentrated under vacuum at 35° C. to 40° C. The IFG free base was dissolved in absolute ethanol (7.7 mL/g residue) and filtered. L-(+)-Tartaric acid (1185 g, 1 g/g residue) was dissolved in absolute ethanol (7.7 mL/g residue), filtered, and slowly added to the solution of IFG in ethanol. This solution was stirred for 45 minutes, filtered, and washed with ethanol (2.5 L, 1 mL/g starting material). The product was dried to constant weight in a vacuum oven at 44° C. IFG tartrate was obtained as a white solid 1.2 kg. $^1$H NMR (300 MHz, D$_2$O): δ 4.40 (s, 2H), 3.70 (dd, J=12, 4 Hz, 1H), 3.66-3.58 (m, 2H), 3.38 (m, 3H), 2.83 (t, J=13 Hz, 1H), 2.79 (t, J=13 Hz, 1H), 1.88-1.77 (m, 1H).

Example 3

Synthesis of IFG Through Dioxane-Fused Xylose

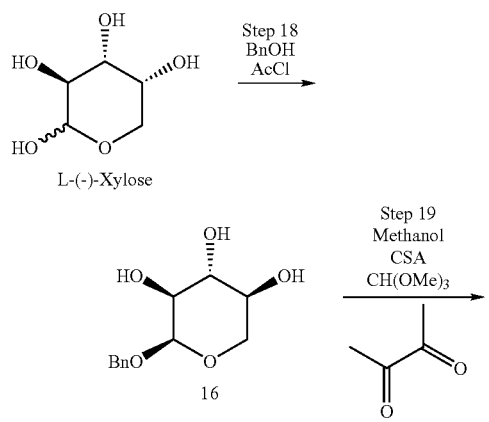

-continued

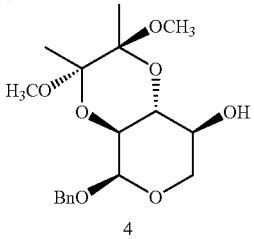

Step 18:

L-xylose (150 g, 1 mol) and benzyl alcohol (450 mL, 4.3 mol) were stirred at 0° C. under nitrogen. Acetyl chloride (30 mL, 0.42 mol) was added at such a rate that the reaction temperature remained at 0° C. The reaction was heated to 40° C. for 16 h and reaction was complete by TLC. Excess benzyl alcohol was removed under reduced pressure. The batch was diluted with MTBE (1200 mL) and cooled to 0° C. for 16 h. The solids were filtered, washed with 350 mL MTBE, and dried under vacuum. Benzyl xylose (16) was obtained as a white solid (118 g, 49%). m.p. 120° C. $^1$H NMR (400 MHz, DMSO-d$_6$): δ 7.40-7.28 (m, 5H), 4.93 (d, 1H, J=4.8 Hz), 4.71 (d, 1H, J=3.6 Hz), 4.82-4.78 (m, 2H), 4.65 (d, 1H, J=12.4 Hz), 4.44 (d, 1H, J=12 Hz), 3.47-3.38 (m, 2H), 3.36-3.27 (m, 3H), 3.25-3.21 (m, 1H).

Step 19:

Benzyl xylose (16, 1 g, 4.2 mmol), 2,3-butanedione (0.4 mL, 4.6 mmol), trimethylorthoformate (1.5 mL, 14.7 mmol), and camphor-10-sulfonic acid (β) (0.116 g, 0.5 mmol) were mixed in methanol (10 mL) under nitrogen at 20° C. The mixture was heated to 60° C. and monitored by TLC until the reaction was complete. The reaction was cooled to room temperature. Solvent was evaporated and the product (4) was obtained by chromatography with 7% ethyl acetate in dichloromethane (427 mg, 29%). $^1$H NMR (300 MHz, CDCl$_3$): identical to the spectrum obtained from inversion of compound 3.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for preparing isofagomine tartrate, comprising protecting the anomeric hydroxyl group of D-(−)-arabinose with a protecting group to form a glycoside; protecting the 2- and 3-hydroxyl groups of said glycoside using a 1,2-dione to form a triprotected arabinose derivative; converting said arabinose derivative to a triprotected xylose derivative; converting said xylose derivative to a triprotected nitrile; converting said nitrile to a protected diol and deprotecting said diol to form isofagomine in the presence of tartaric acid.

2. The method of claim 1 further comprising converting said arabinose derivative to said xylose derivative through an activated system wherein said activated system is optionally isolated before conversion.

3. The method of claim 1 further comprising converting said xylose derivative to said nitrile using an activated system, wherein said activated system is optionally isolated before conversion followed by displacement by a cyano source.

4. The method of claim 1 further comprising obtaining said nitrile after purifying said xylose derivative.

5. The method of claim 1 further comprising converting said arabinose derivative to said xylose derivative by a Mitsunobu inversion reaction to form an inverted ester derivative and saponification.

6. A method for preparing isofagomine tartrate, comprising protecting the anomeric hydroxyl group of D-(−)-arabinose with a protecting group to form a glycoside; protecting the 2- and 3-hydroxyl groups of said glycoside using a 1,2-dione to form a triprotected arabinose derivative; converting said arabinose derivative to a triprotected xylose derivative; converting said xylose derivative to a triprotected nitrile; converting said nitrile in the presence of tartaric acid to a protected isofagomine tartrate salt and deprotecting said isofagomine tartrate salt.

7. A method for preparing isofagomine tartrate, comprising protecting the anomeric hydroxyl group of D-(−)-arabinose with a protecting group to form a glycoside; protecting the 2- and 3-hydroxyl groups of said glycoside using a 1,2-dione to form a triprotected arabinose derivative; converting said arabinose derivative to a triprotected xylose derivative; converting said xylose derivative to a triprotected nitrile; reducing said nitrile to a triprotected primary amine; deprotecting said primary amine to a diol; and subjecting the diol to catalytic hydrogenation in the presence of tartaric acid.

8. The method of claim 1 wherein protecting of said anomeric hydroxyl group of D-(−)-arabinose is accomplished using an alcohol, an activating agent and optionally a solvent; and formation of said arabinose derivative is accomplished using an acid and an alcohol.

9. The method of claim 6 wherein protecting of said anomeric hydroxyl group of D-(−)-arabinose is accomplished using an alcohol, an activating agent and optionally a solvent; and formation of said arabinose derivative is accomplished using an acid and an alcohol.

10. The method of claim 7 wherein protecting of said anomeric hydroxyl group of D-(−)-arabinose is accomplished using an alcohol, an activating agent and optionally a solvent; and formation of said arabinose derivative is accomplished using an acid and an alcohol.

* * * * *